(12) United States Patent
Nisani et al.

(10) Patent No.: US 9,237,839 B2
(45) Date of Patent: Jan. 19, 2016

(54) DEVICE, SYSTEM AND METHOD FOR ACTIVATION, CALIBRATION AND TESTING OF AN IN-VIVO IMAGING DEVICE

(75) Inventors: Micha Nisani, Ramot Itzhak (IL); Ido Bettesh, Zichron Ya'akov (IL); Boaz Aizenshtark, Shimshit (IL); Eli Horn, Kiryat Motzkin (IL)

(73) Assignee: GIVEN IMAGING LTD., Yoqneam Ilite (IL)

( * ) Notice: Subject to any disclaimer, the term of this patent is extended or adjusted under 35 U.S.C. 154(b) by 554 days.

(21) Appl. No.: 13/515,816

(22) PCT Filed: Dec. 16, 2010

(86) PCT No.: PCT/IL2010/001068
§ 371 (c)(1),
(2), (4) Date: Jun. 14, 2012

(87) PCT Pub. No.: WO2011/073987
PCT Pub. Date: Jun. 23, 2011

(65) Prior Publication Data
US 2012/0262560 A1    Oct. 18, 2012

Related U.S. Application Data

(60) Provisional application No. 61/287,373, filed on Dec. 17, 2009.

(51) Int. Cl.
*A61B 1/04* (2006.01)
*A61B 1/06* (2006.01)
(Continued)

(52) U.S. Cl.
CPC ............. *A61B 1/041* (2013.01); *A61B 1/045* (2013.01); *H04N 2005/2255* (2013.01); *H04N 2201/0079* (2013.01)

(58) Field of Classification Search
CPC .......... A61B 1/04; A61B 1/041; A61B 5/073; A61B 5/6861; H04N 2005/2255
See application file for complete search history.

(56) References Cited

U.S. PATENT DOCUMENTS

| 4,278,077 A | 7/1981 | Mizumoto |
| 5,604,531 A | 2/1997 | Iddan et al. |

(Continued)

FOREIGN PATENT DOCUMENTS

| DE | 344 0177 | 11/1984 |
| JP | 4109927 | 4/1992 |

(Continued)

OTHER PUBLICATIONS

International Search Report of Application No. PCT/IL2010/001068 mailed on May 25, 2011.

*Primary Examiner* — Joseph Ustaris
*Assistant Examiner* — Rebecca Volentine
(74) *Attorney, Agent, or Firm* — Pearl Cohen Zedek Latzer Baratz LLP

(57) ABSTRACT

A device, system, and method for activating and initializing an in vivo imaging device with an RF radiation signal. Functionality of the in vivo imaging device is tested and results may be reported to a user. The in vivo imaging device may include an RF switch to facilitate powering or deactivation of one or more electrical components of the device. The initialization system may include an optical artifact testing unit, a field of illumination testing unit, and a transmission/reception testing unit. The activation system may comprise an in vivo device association unit which may relate a designated device to a single data recorder or to a single controller.

20 Claims, 10 Drawing Sheets

(51) Int. Cl.
*A61B 1/045* (2006.01)
*H04N 5/225* (2006.01)

(56) References Cited

U.S. PATENT DOCUMENTS

| | | | |
|---|---|---|---|
| 5,993,378 A | | 11/1999 | Lemelson |
| 6,240,312 B1 | | 5/2001 | Alfano et al. |
| 6,734,958 B1 | * | 5/2004 | MacKinnon et al. ......... 356/236 |
| 7,009,634 B2 | | 3/2006 | Iddan et al. |
| 7,280,141 B1 | * | 10/2007 | Frank et al. .................. 348/243 |
| 7,295,226 B1 | | 11/2007 | Meron et al. |
| 7,354,397 B2 | | 4/2008 | Fujita et al. |
| 7,931,149 B2 | | 4/2011 | Gilad et al. |
| 8,262,566 B2 | | 9/2012 | Gilad et al. |
| 2002/0103417 A1 | | 8/2002 | Gazdzinski |
| 2003/0007672 A1 | * | 1/2003 | Harman et al. ............... 382/128 |
| 2004/0155957 A1 | * | 8/2004 | Kobayashi ..................... 348/68 |
| 2006/0155174 A1 | * | 7/2006 | Glukhovsky et al. ......... 600/301 |
| 2007/0118012 A1 | | 5/2007 | Gilad |
| 2007/0129602 A1 | | 6/2007 | Bettesh et al. |
| 2007/0142707 A1 | * | 6/2007 | Wiklof et al. ................. 600/118 |
| 2008/0027284 A1 | * | 1/2008 | Suda ............................. 600/134 |
| 2008/0045792 A1 | | 2/2008 | Shimizu et al. |
| 2008/0103372 A1 | | 5/2008 | Segawa |
| 2008/0228031 A1 | * | 9/2008 | Leiner et al. .................. 600/109 |
| 2008/0240558 A1 | * | 10/2008 | Li et al. ......................... 382/167 |
| 2008/0255635 A1 | | 10/2008 | Bettesh et al. |
| 2008/0262304 A1 | | 10/2008 | Nisani et al. |
| 2009/0213211 A1 | * | 8/2009 | Bayer et al. .................... 348/65 |
| 2010/0073528 A1 | * | 3/2010 | Lee et al. ....................... 348/255 |

FOREIGN PATENT DOCUMENTS

JP 1992-144533 5/1992
WO WO 2008/030472 3/2008

\* cited by examiner

DEVICE, SYSTEM AND METHOD FOR ACTIVATION, CALIBRATION AND TESTING OF AN IN-VIVO IMAGING DEVICE

CROSS-REFERENCE TO RELATED APPLICATIONS

This application is a National Phase Application of PCT International Application No. PCT/IL2010/001068, International Filing Date Dec. 16, 2010, entitled "Device, System and Method for Activation, Calibration and Testing of an In-Vivo Imaging Device", published on Jun. 23, 2011 as International Patent Application Publication Number WO 2011/073987 claiming priority from U.S. Provisional Patent Application No. 61/287,373, filed Dec. 17, 2009, each of which is incorporated herein by reference in its entirety.

FIELD OF THE INVENTION

The present invention relates to ingestible imaging devices, and more particularly to a device for activating an ingestible imaging device using radio frequency radiation, and for testing and correcting parameters of an ingestible imaging device.

BACKGROUND OF THE INVENTION

In-vivo sensing devices, such as for example ingestible in-vivo imaging capsules, may include an autonomous power source such as, for example, a battery whose power may last for a limited period of time in use. To conserve power, it may be preferable to turn on the in-vivo sensing device only a short time before the device is ingested or swallowed. Typically, the battery and all other components of the in-vivo sensing device may be sealed in the in-vivo sensing device during manufacturing to ensure, for example, durability and water-tightness of the in-vivo device. Such a sensing device may not accommodate a manual or externally accessible switch or mechanism for operating the device after it is sealed. Quality control standards may still require that each in-vivo sensing device be tested prior to its use/ingestion, where the testing may require that the device be activated and deactivated possibly several times prior to an in-vivo operation.

Different types of activation switches of in vivo sensing devices are known. Magnetic switches similar to the switch described in U.S. Pat. No. 7,295,226 to Meron et al. may be used. However, when an external magnet creates a magnetic field near the device after activation, the device may be accidentally switched off. For example, during magnetic maneuvering of the in vivo device by an external magnetic field, an activation method of the in vivo device which is not interfered with by the external magnet may be required.

Temperature switches are also known, for example as described in US Patent Application Publication Number 2008/0045792, which discloses activating a capsule based on, for example, a change in temperature at the time of introduction into the inside of the body of a subject from the outside of the body of the subject, thereby preventing actuation of the capsule apparatus outside the body of the subject. However, such temperature switches may accidentally be actuated outside of the body, for example during storage or transportation periods, in cases of high environmental temperatures such as 38-40° Celsius, which are not uncommon in extensive regions of the globe.

In-vivo imaging devices may include RF switches to activate the device prior to use. RF switches, for example as disclosed in US Patent Application Publication Number 2007/0129602, may require an activating unit to create an electromagnetic (EM) signal which may activate and/or deactivate the RF switch.

In vivo imaging procedure activation methods may include light correction, identification of a specified mark, white balance calibration, for example as described in U.S. Pat. No. 7,295,226 to Meron et al.

In some cases, for example in hospitals or clinics, several patients may undergo in vivo procedures at the same time, thus multiple in vivo devices may be operating during the same time period. A single recording device may receive data sent from more than one in vivo device. In case of two-way communication between the in vivo device and a data recorder or a controller, a single in vivo device may receive control data from more than one controller. For example, US Patent Application Publication Number 2008/0255635 discloses associating a specific in vivo sensing device to images received in a data recorder.

It would be beneficial to provide a system and procedures for testing the potential quality of images captured by in vivo imaging devices prior to the ingestion thereof, because light reflections, which may be caused by imprecise optical system alignment or by roughness of an optical window, and artifacts that may be caused by scratches and other defects that may obstruct portions of captured scenes, may degrade the quality of captured images.

SUMMARY OF THE INVENTION

According to one embodiment, an initialization system for initializing an in-vivo device is provided. The in-vivo device may include one or more imaging units or imaging systems, a radio frequency (RF) activation switch, one or more illumination sources and a transceiver to transmit, for example, image data and other types of data, and to receive data (e.g., commands, indications, etc.). The initialization system may include (1) an initialization unit which may include a recessed space, or open or closed chamber, for positioning therein the in vivo device, and (2) an (RF) activation unit for RF activation of the in vivo device. The activation unit may include an RF radiation source for generating an RF signal which may be used to activate the in vivo device, and an operating switch to activate the RF radiation source. The operating switch may be, for example, user-operable. In addition, an external data recorder may receive a signal or image data from the activated in-vivo device. The signal that the data recorder may receive from the in-vivo device may include an identification ("ID") code of the in-vivo device, such as a unique number or ASCII string. An in-vivo device association unit may associate the in-vivo device with the data recorder. The in-vivo device association unit may functionally be coupled to, or be an integral part of the data recorder or activation unit. The device association unit may accept or receive the ID code of the in-vivo device and ID data of the data recorder, and use the ID code and ID data to associate the two devices, for example in order to enable the in-vivo device to communicate only with (e.g., receive and respond to control data that is transmitted only from) the associated data recorder, or in order to enable the data recorder to receive and respond only to data that was sent from the in-vivo device associated with it. In some embodiments, a device functionality test unit may test one or more functionalities of the in-vivo device. An indicator or a display may display to a user a result of the device functionality test. In some embodiments, the device functionality test unit may include and use an optical target to produce or generate an illumination reference map of, or that represents, the illumination profile of the illumination sources of the in-vivo device. In some embodiments, the device functionality test unit may include and use an optical target to produce an optical artifact map of the imaging unit/system.

The device association unit may limit the exchange (e.g., transmission and reception) of data between the designated in-vivo device and the data recorder. For example, an ID code of the designated in-vivo device may be input by a user to the data recorder before an in vivo procedure is started or commenced.

A transceiver may be provided, for example as a standalone transceiver, or as a transceiver which may be included in the activation unit or in the data recorder. The transceiver may test or monitor transmission parameters and/or reception parameters of, or associated with, the designated in-vivo device, for example transmission strength, received signal strength, etc, in order to verify proper function of the transmission and reception capabilities of the system.

According to one embodiment, a method for activating and testing an in-vivo device is provided. The in-vivo device may include one or more imaging systems or units, an RF switch, one or more illumination sources and a transceiver. The method may include placing a dormant (e.g., an inactivated) in-vivo device in a predetermined position in, or in a light-tight chamber of, an (RF) activation unit, and transmitting an RF signal from/by the RF activation unit to activate the in-vivo device. The method may also include a step of detecting a connection between a data recorder and the RF activation unit, and associating the data recorder to the activated in vivo device.

Functionality of the in-vivo device may be tested prior to its ingestion by using the RF activation unit and/or the data recorder. For example, the in-vivo device may generate, produce or obtain an illumination reference map by capturing, for example, an image of a white target (e.g., white board, white sheet, and the like), and the illumination reference map may indicate the illumination intensity level of various pixels in the imaging sensor/array at the time of the white target capturing. One or more illumination/light sources that make up the illumination source of the in-vivo device, or the illumination source as a whole, may be calibrated or adjusted to produce a predetermined, desired, or optimal field of illumination ("FOI"), for example, according to, or contingent on, a predetermined or previously obtained illumination reference map. An image gain level used to capture images by the in-vivo device may be controlled and adjusted based on the illumination reference map. In another example, an optical artifact map may be obtained by the in-vivo device, for example by capturing a reference image of an optical artifact reference target. The optical artifact map may be analyzed by a processing unit, and a presence of an artifact in the optical artifact map may be determined. For example, the optical artifact map may be analyzed to determine the percentage of faulty areas in the field of view ("FOV") of the in-vivo device. The identified artifacts may be substantially removed from captured images at a later stage, for example by subtracting the optical artifact map from the captured images. In yet another example, parameters of transmission and/or reception of the in-vivo device, or transmission and/or reception between the in-vivo device and the associated data recorder, may be tested. Results of one or more functionality tests may be provided to a user, using a dedicated display or indicator, or for example using an integrated display which may be included in the data recorder or activation unit. In some embodiments, if one or more functionality tests fail, the in-vivo device may be deactivated, for example automatically, and an indication of device activation failure may be provided or signaled to a user.

BRIEF DESCRIPTION OF THE DRAWINGS

The present invention will be understood and appreciated more fully from the following detailed description taken in conjunction with the drawings in which.

Figure 1:
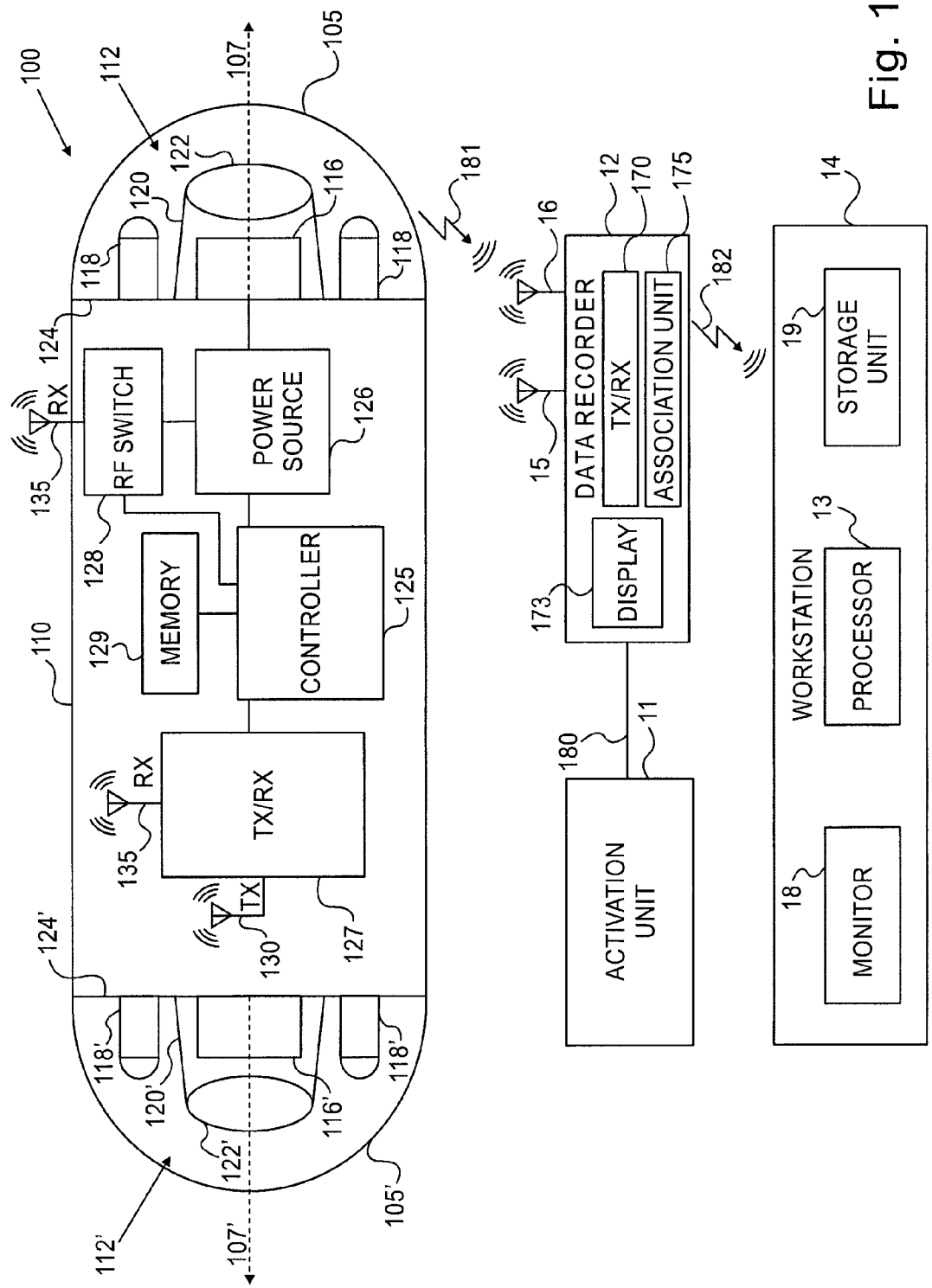
FIG. 1 is a simplified conceptual illustration of an in-vivo imaging system including an external RF activation unit according to an example embodiment.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Reference is made to FIG. 1, showing a simplified conceptual illustration of an in-vivo imaging device 100 with an external RF activation unit 11 and an in vivo device association unit 175 according to an embodiment of the present invention. Device 100 may be an autonomous in-vivo sensor, for example, an in-vivo imaging device such as a swallowable capsule, with one or more imaging units/systems for gathering data in-vivo. An activation unit 11 may remotely activate device 100 from a dormant state prior to ingesting or inserting device 100 in-vivo. When activated, device 100 may gather data in-vivo and may transmit data by one or more transmitting antenna/s 130 to an external data recorder 12. Device 100 may receive data, for example data sent from the data recorder 12, using one or more receiving (Rx) antenna/s 135. Data recorder 12 may include one or more receiving antennas 15, and optionally one or more transmitting antennas 16. In some embodiments, the same antenna may be used for reception and transmission. Data recorder 12 may typically include a recorder and storage unit to record and store received data and may optionally include processing and control capabilities. In some embodiments, external data recorder 12 may transmit for example control and/or calibration data to device 100 through transmission antenna 16. Data recorder 12 may include an association unit 175, which may enable, for example, one-to-one association of in-vivo imaging device 100 to data recorder 12. Such association between a designated device and a specific data recorder may prevent erroneous reception and consideration of communication of a an in-vivo device by a data recorder that it is not associated with that in-vivo device which may be simultaneously operating in the same area, for example in a hospital or clinic where multiple in-vivo imaging procedures may be performed simultaneously. Association unit 175 may include a memory unit to store a unique ID code of the associated in-vivo device 100. The memory unit may be a separate component, or may be included, for example, in a TX/RX unit 170 or in a storage unit (not shown) of data recorder 12. TX/RX unit 170 may further include a processing unit, and an RF module which may include, for example, a receiver/transmitter, a modem, etc. Association unit 175 may use a transceiver of data recorder 12 to receive the unique ID code transmitted by the in-vivo device 100. In some embodiments, association unit 175 may be included in TX/RX unit 170 of data recorder 12.

In one embodiment activation unit 11 may be detachably connected to data recorder 12, for example by a connection 180 which may be for example, a cable connection such as a USB connection, or a wireless connection such as WI-FI, WLAN, cellular, Bluetooth, etc. In another embodiment of the present invention, data recorder 12 and activation unit 11 may be integrated into a single unit, for example, may be integrated into a single portable unit. Activation unit 11 may generate image calibration data, which may include, for example, illumination reference image data and/or optical artifact image data. The reference image data may be transmitted or transferred to data recorder 12, which may store the reference image data and/or use it to process image data received from device 100. In some embodiments, reference image data produced by activation unit 11 may be sent to workstation 14 and may be used to produce improved images from the image data received from device 100, e.g. clearer images without artifacts, or uniformly illuminated images as will be explained hereinbelow.

Data captured by device 100 and received by data recorder 12 may be, for example downloaded to workstation 14 for processing, analysis and display, for example by display unit 18. The data may be transferred through connection 182 which may be any wired or wireless connection, e.g., a cable USB connection, or wireless connection such as WI-FI, WIMAX, WLAN, cellular, Bluetooth, etc. In one embodiment of the present invention, data recorder 12 and workstation 14 may be integrated into a single unit, for example, may be integrated into a single portable unit. In other embodiments data recorder 12 may be capable of transmitting signals to device 100 as well as receiving, for example using transmitting antenna/s 16. In yet another embodiment of the present invention, data recorder 12 may include display capability, for example data recorder 12 may include a real-time display device 173, for example as disclosed for example in US Patent Application Publication Number 2008/0262304 to Nisani et al.

In-vivo device 100 may be an in vivo imaging capsule, such as for example a PillCam® swallowable video capsule manufactured by Given Imaging Ltd. In-vivo device 100 may include one or more sensing devices such as, for example, one or more imaging systems such as imaging systems 112, 112' within an outer covering or housing 110 and an optical dome 105, constructed and operative in accordance with an embodiment of the invention. Where contextually appropriate, the terms "imaging unit" and "imaging system" are interchangeably used herein. Housing 110 may be, for example, spherical, ovoid, or any other suitable shape and may be partially deformable. Imaging system 112 may typically include at least an imager 116, which may be or may include a charge coupled device (CCD), a complementary metal oxide semiconductor (CMOS) imager, another suitable solid-state imager or other imagers. Imaging system 112 may also include a lens assembly 122, a lens assembly holder 120, and one or more illumination sources 118 (e.g., a pair of singular illumination sources, an illumination ring, etc.), such as for example, light emitting diodes (LEDs), for illuminating the areas to be imaged by imager 116. Likewise, imaging system 112' may include at least an imager 116', a lens assembly 122', a lens assembly holder 120', and one or more illumination sources 118'. One example of a LED illumination source which may be used is NESW007 LED manufactured by Nichia Corporation of Japan. Other positions for imagers 116, 116', illumination sources 118, 118' and other components may be used and other shapes of a housing 110 may be used.

Illumination sources 118, 118' may vary in strength and in the produced field of illumination (FOI), for example due to variations and inaccuracies of the illumination source, for example due to variances during production, or in its positioning during the assembly processes. Furthermore, inaccuracy of the positioning of illumination sources 118 inside imaging device 100 may be caused by one or more of several factors, such as: tolerance of the assembly process of the illumination unit 118, 118' (e.g. LED) on the electrical circuit, tolerance of the exact position of the die which produces the light inside the illumination unit 118, 118', and/or tolerance of the positioning of the dome 105, 105' for example with respect to, for example, to circuit board 124, 124', or viewing window in relation to the imaging system 112, the optical axis 107, 107' and the illumination unit 118, 118'. These factors may contribute to an accumulated error in the placement of the illumination unit 118, which may cause stray light reflections from the viewing window or dome 105, and an inconsistent (e.g., non-uniform, or non-linear) FOI. LEDs (Light Emitting Diode) which may typically be used as illumination units, are intrinsically imprecise components which may vary, for example, in their illumination intensity, physical size, angle of the die in its LED package, and position of the die relative to its package. Such illumination source typically causes stray light to hit the dome 105, 105' of imaging device 100, and reflect back to the imager 116, 116', possibly causing artifacts such as bright white spots and partial obstruction of the image.

Such variations may create an uneven field of illumination for example in an imaging device with a plurality of illumination sources. As a result, the quality of the produced images of device 100 may be reduced, since some regions of the images may be overly illuminated (e.g., reflecting saturating amount of light onto the respective region in the imager) while other regions of the image may be poorly illuminated, making it difficult to observe objects in the image, e.g. polyps, lesions or other pathologies. According to one embodiment of the present invention, a possible solution to this problem may include capturing an illumination reference map or reference image of the illumination sources 118, 118', and correcting the non-uniform illumination of the captured image after the images are stored. According to one embodiment, the amount of energy or current (continuous or average) delivered to each illumination source may be controlled, according to the measured illumination intensity level produced by an illumination unit, for example by providing more current to an illumination source which is weaker, and less current to an illumination source which is stronger, thereby balancing the illumination levels of different illumination units and creating a uniform illumination of the captured scene. In some embodiments, these solutions may be combined. For example, a reference illumination image may be used to calibrate the amount of energy provided to an illumination unit such that the illumination unit will provide a predetermined illumination level.

Device 100 may include and/or contain one or more power units 126, a transceiver 127, e.g. an RF transmitter/receiver, and one or more antennas 130, 135 for transmitting and/or receiving data, e.g. receiving control data. In some embodiments one or more antennas 130 may be used for transmitting data and one or more antennas 135 may be used for receiving data. In some embodiments a separate antenna (not shown) may be used to receive the RF activation/deactivation signal from activation unit 11. Antennas 130 and/or 135 may transmit/receive data using the same frequency or using different frequencies. For example, the transmission frequency used by Tx antenna 130 may be 434 MHz, and the reception frequency used by Rx antenna 135 may be 13.56 MHz. Other frequencies are possible, and in some embodiments the same frequency may be used both for transmission and for reception in device 100. However, in some embodiments, a single antenna may be used to receive control data and RF activation/deactivation signals from activation unit 11 and/or from recorder 12. Power unit 126 may include an independent or portable power source such as one or more batteries and/or other suitable power sources. In another example power unit 126 may include a power induction unit that may receive power from an external source. In one example, transceiver 127 may include control capability, for example transceiver 127 may be or may include a controller for controlling various operations of device 100, although the control capability or one or more aspects of the control may be included in a separate component such as for example controller 125 or other circuitry elements which may be included in device 100. Transceiver 127 may typically be included on an Application Specific Integrated Circuit (ASIC), but may be of other constructions.

Device 100 may include a processing unit separate from transceiver 127 that may, for example, contain or process instructions. In some embodiments, power unit 126 may include, wholly or partially, the components of a mechanically static RF operable RF switch 128 that may control activation of device 100, for example powering of transceiver 127, imager 116 and illumination source 118. Other components may be activated directly or indirectly by RF switch 128. In other embodiments, RF switch 128 may be a separate unit, or may be included or partially included in transceiver 127 or in another component of device 100, e.g. controller 125. A receiving antenna 135 may be connected to the RF switch 128 in order to receive the activation signal from an external activation unit. RF switch 128 may be similar to an RF switch described, for example, in FIG. 4 of US Patent Application Publication Number 2007/0129602. RF switch 128 may be used to activate and/or to deactivate and/or to control in-vivo device 100 or components of in-vivo device 100 on demand. In one example, one or more low power components of in-vivo device 100 may be powered during the dormant state of in-vivo device 100 to facilitate waking up of transceiver 127 on demand. According to one embodiment, it may be desirable to maintain in-vivo device 100 in a dormant state prior to use so as not to deplete power source 126 prematurely. During the dormant state, in-vivo device 100 may consume a relatively low power from power source 126.

In some embodiments, device 100 may include a device memory 129, which may be a non-volatile memory such as, for example, a read-only memory or a flash memory. The device memory 129 may be a register incorporated into a controller 125 or transceiver 127.

In-vivo device 100 may be inserted in-vivo, for example by swallowing or ingesting. In-vivo device 100 may enter a body lumen for in-vivo imaging and may be, for example, fixed at a position in the body or it may move through, for example, a gastrointestinal (GI) tract or other body lumen. Device 100 may include components and operate similarly to the imaging systems described in U.S. Pat. No. 7,009,634 to Iddan, et al. and/or US Patent Application Publication Number US 2007/0118012, entitled "Method of assembling an in-vivo imaging device", published on May 24, 2007, both assigned to the common assignee of the present application. Furthermore, a reception, processing and review system may be used, such as in accordance with embodiments of U.S. Pat. No. 7,009,634, although other suitable reception, processing and review systems may be used.

In one embodiment, components of in-vivo device 100 may be sealed, e.g. water and air tightly sealed, within the housing 110. For example, imager 116, illumination sources 118, power source 126, transceiver 127, receiving and/or transmitting antennas 130, 135 and circuit board 124, may be sealed and/or contained within the watertight housing 110.

In-vivo device 100 may be a capsule or other unit that does not require wires or cables external to device 100, for example, to receive power or transmit/receive data/information. For example, power may be provided to in-vivo device 100 internally, by an internal battery. Other embodiments may have other configurations and capabilities. In-vivo device 100 may receive control information and other information from an external source, for example from data recorder 12 or activation unit 11. In-vivo device 100 may initially be in a dormant state and may be activated and/or woken up prior to ingesting by transferring to device 100, for example by transmitting to it, a signal having a predefined level and/or an RF signal having a predefined pattern. A modulated RF signal generated outside device 100 may induce energy in one or more receiving (Rx) antennas 135 and transmit a signal to RF switch 128 to activate/operate device 100. In an alternate embodiment, RF switch 128 may also be used to deactivate device 100.

Figure 2:
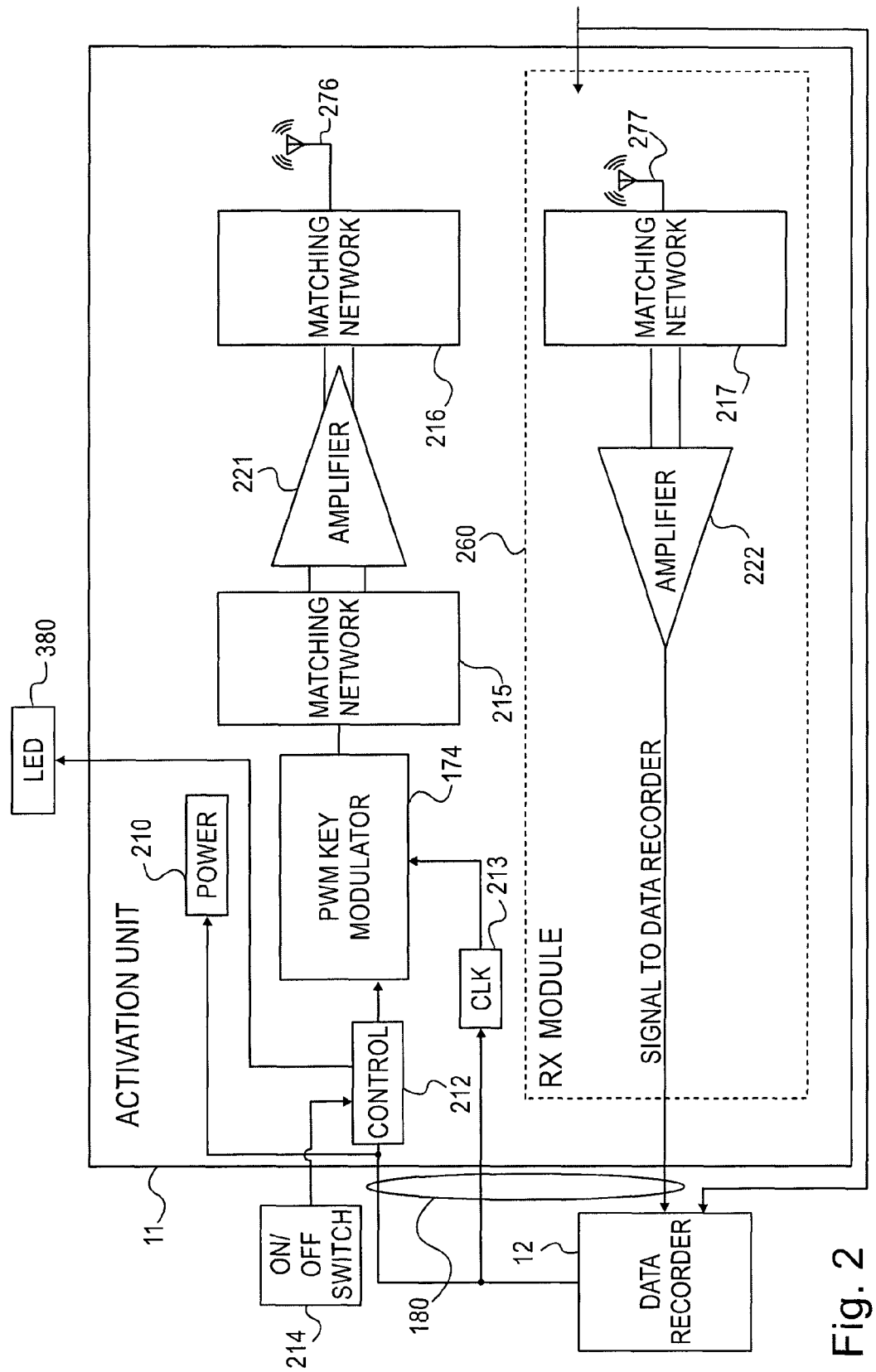
FIG. 2 is a simplified diagram of an exemplary circuit diagram of an RF activation unit according to an example embodiment.

Reference is made to FIG. 2 showing a simplified block diagram of an activation unit 11 that may be used to generate a modulated RF signal to activate and/or deactivate device 100 prior to ingesting device 100 and/or prior to inserting the device 100 in-vivo. In one example, activation unit 11 may generate a predetermined modulated RF signal for activating, turning on, or deactivating device 100, or waking up device 100 from a dormant state. Activation unit 11 may comprise a pulse width modulation ("PWM") key modulator 174 for generating the required or predetermined modulated RF signal. According to one embodiment of the present invention, the generated RF signal may have a predetermined pattern. For example, a first predefined pattern may give indication to RF switch 128 to wake device 100 up and a second predefined pattern may give indication to RF switch 128 to return device 100 to a dormant state. The number of activations and deactivations of device 100 may be unlimited. Other signals may be implemented to control the operational state, e.g. the power state, or the functional state of device 100. According to one embodiment of the present invention, an electrically powered antenna 276, for example a coil antenna, may generate an RF radiation signal when current flows through antenna 276. Activation unit 11 may include a controller 212 to control the operation of activation unit 11. Controller 212 may be used to toggle in-vivo device 100 from a dormant state to an operationally active state, and vice versa. Current flow may be initiated by activating controller 212 and/or operating an ON/OFF switch 214, which may include for example, a button or dial switch, and may enable a user to select which signal to generate. For example, a predetermined activation signal or a predetermined deactivation signal may be generated by PWM key modulator 174, and may be transmitted to device 100 using antenna 276. PWM key modulator 174 may include an on/off keying unit which may produce, by using on/off keying, the pulse width modulation (PWM) according to the predetermined signal that is to be generated. A clock 213 may produce, or may facilitate production of, a carrier radio frequency ("RF") signal having a fixed frequency, and activate, trigger or use, a state machine to modulate the carrier RF signal. In some embodiments, clock 213 may receive the carrier RF signal, or an instruction to produce a carrier RF signal, from data recorder 12. The PWM modulated RF signal may be sent to an impedance matching unit (e.g., matching network 215), in order to maximize power transfer and minimize reflectance (e.g., reflections from the load of PWM key modulator 174; e.g., the input impedance of amplifier 221). Amplifier 221, for example a differential amplifier or a single-ended amplifier, may be used for amplifying the signal originating from PWM key modulator 174. Optionally, an additional impedance matching unit 216 may be used before the signal is transferred to the antenna 276 for transmission to device 100. Impedance matching units 215, 216 may include combinations of transformers, resistors, inductors and/or capacitors. Other methods for generating an RF signal may be used, and any modulation scheme may be used to modulate the RF signal. The data modulating the RF activation signal may preferably be sufficiently robust in order to prevent accidental activation of the RF switch 128 by incidental RF signals which may be picked up by receiving antenna/s 135. In order to verify that the in-vivo device is not erroneously activated by an incidental RF signal, data that modulates the RF activation signal may be compared to a specific predetermined waveform (e.g., waveform template), which may be stored, for example, in a memory unit of device 100. By way of example, the predetermined waveform may be a chirp signal.

Activation unit 11 may include power source 210, for example, a DC power source, e.g. a battery that may power activation unit 11. In some embodiments, activation unit 11 may not require an independent power source, and may receive power from an external power unit, or from data recorder 12.

A LED indicator 380, or a different type of visual/audio indicator, may be used to provide an indication to the user regarding the state of activation unit 11 and/or the state of device 100. For example, when activation unit 11 generates an activation signal, LED indicator 380 may blink. When device 100 is activated, LED indicator 380 may output a steady light, or another indicator may indicate to the user that device 100 is activated, for example by using a different color LED or displaying a message, for example on display 173 of data recorder 12 which may be connected to activation unit 11 during activation of device 100. Other methods of indicating the status of device 100 may be used.

According to one embodiment of the present invention, activation unit 11 may operate in frequencies that may be typical to frequencies used by RFID tags. For example, typical frequencies may include 13.56 MHz, 27.12 MHz, 434 MHz, 865 MHz, and 2.45 GHz. Other RFID frequencies or other suitable frequencies may be used. In some embodiments, antenna 276 may be included in a parallel resonance circuit or in a serial resonance circuit that may include, for example, a capacitor. The resonant circuit may be tuned, for example, to have the same resonance frequency as the resonant circuit 409 (shown in FIG. 4).

Activation unit 11 may include an electronic circuit for transferring energy from a primary coil to a secondary coil, where antenna 276 may be, or be part of, the primary coil that may induce energy in a secondary coil that may be, for example, Rx antenna 135 within in-vivo device 100. Other suitable circuitries may be used to generate and transmit an RF signal to operationally activate in-vivo device 100. According to one embodiment of the present invention, in-vivo device 100 may be inserted into a concave space (e.g. concave space 310 as in FIG. 3A) or into a lightproof chamber (e.g., chamber 312 as in FIG. 3B), which may be surrounded by antenna 276 for activation. When in-vivo device 100 is placed in, or accommodated in, the recessed space or closed chamber, antenna 276 and Rx antenna 135 may be positioned relative to each other such that the maximum and/or sufficient amount of electrical energy, for example in the form of electromagnetic radiation, may be induced or transmitted from antenna 276 to Rx antenna 135. For example, in-vivo device 100 may be inserted into the recessed space such that internal Rx antenna 135 of in-vivo device 100 may be substantially parallel or co-linear with antenna 276. For example, antenna 135 may be a coil antenna that may be positioned in parallel to a larger coil which may make up antenna 276. Antenna 276 may be formed as a loop, surrounding the concave section 310, or chamber 312, accommodating in-vivo device 100. In other embodiments, a different orientation of internal Rx antenna 135 relative to activated antenna 276 may be required for activation of in-vivo device 100. In yet other embodiments, no specific orientation may be required at all. In some embodiments, in-vivo device 100 may be placed substantially within the concave space 310, or chamber 312, surrounded by antenna 276, and the RF radiation generated within the coil of antenna 276 may induce energy in Rx antenna 135 within in-vivo device 100 to a level that may activate RF switch 128 within in-vivo device 100.

Upon activation of RF switch 128 within in-vivo device 100, RF switch 128 may retain the in-vivo device in the active state subsequent to its activation, or RF switch 128 may maintain the active state until an additional and/or alternate RF signal, e.g. RF radiation pattern, is received by RF switch 128. For example, the power provided to one or more electrical components of in-vivo device 100 as a result of the activation of RF switch 128 may be provided subsequent to termination of the RF signal. After activation, in-vivo device 100 may be ingested for capturing and transmitting in-vivo data (e.g., image data) through one or more in-vivo body lumens.

In one embodiment, antenna 276 may additionally be used to sense the status, for example the operating mode, of device 100 inserted to a recessed space surrounded by antenna 276, such as an image capturing mode, imager disabled (sleep, or dormant) mode, high frame rate mode, low frame rate mode and/or energy-saving mode. For example, antenna 276, or another component of activation unit 11, may also act as a receiving antenna that may pick up signals transmitted by in-vivo device 100, e.g. signals indicating the operational mode of in-vivo device 100. In some embodiments activation unit 11 may include a separate receiving module 260, which may include antenna or coil 277, an impedance matching unit 217 and amplifier 222, which may be part of a receiving circuit that may allow receiving signals by activation unit 11. These received signals may be used by activation unit 11, and/or transmitted to another device, e.g. data recorder 12 or workstation 14. Other signals may be picked up and, for example, processed to indicate, for example, an operational status of in-vivo device 100.

In one embodiment of the present invention, activation unit 11 may be detached from units/elements 12, 14, 300, and/or 310 (e.g., a stand-alone unit), and may be portable or suitable for placement on a desk top. In other embodiments of the present invention, activation unit 11 may be integral to an initialization unit 300, a data recorder 12 or workstation 14, and may take other suitable forms. In another example, activation unit 11 may be integral to the packaging of in-vivo device 100, and opening of the packaging may initiate operation of activation unit 11. Other configurations may be used.

In some embodiments, activation unit 11 may be connected, for example by cable 180, or by wireless interface, to, or may be integrated into, data recorder 12 or to/into workstation 14. If activation unit 11 is connected to data recorder 12; e.g., via connection 180, receiving module 260 may not be required because data captured by in-vivo device 100 and directly transferred by it to data recorder 12 may then be transferred from data recorder 12 to activation unit 11 directly (i.e., without receiving it by receiving module 260). Activation unit 11 may automatically detect the connection to data recorder 12, for example using a USB protocol when connection 180 is a USB-type connection. Other types of communication interfaces may be used, such as other types of serial connections or parallel connections, or wireless connections e.g. Bluetooth, wireless LAN, Wi-Fi, WiMAX, GSM, etc. The process of detecting a connection between activation unit 11 and data recorder 12 depends on the type of communication interface used by them, and it would typically involve using some kind of handshaking.

In some embodiments, activation unit 11 may issue an audible signal, such as a ring or tone, to indicate that device 100 has been turned on or activated. Activation unit 11 may evaluate the functions or functionality of a device, such as in-vivo device 100, which is activated to determine whether the device is operating properly/as planned. For example, activation unit 11 may evaluate whether a battery or power source inside in-vivo device 100 is operating or operational. In some embodiments, device 100 may wake up from a dormant state and transmit a response signal. The response signal may include a predetermined wave pattern or data, and may be received by activation unit 11, for example by optional receiving module 260. The response signal may be evaluated, for example, by a processor or controller in activation unit 11, or may be transmitted to data recorder 12 or workstation 14 for processing and/or evaluation. The response signal may include or indicate, for example, the power state of power source 126 of in-vivo device 100. The current consumed from power source 126 may be evaluated, for example compared to a threshold level, and, based on the evaluation result, it may be determined whether power source 126 has enough power to enable imaging device 100 to complete an in vivo procedure. A message or other indication, for example an error code indicating that imaging device 100 has insufficient power to complete an in vivo procedure, may be displayed to a user on an optional display device, e.g. display 173 of data recorder 12 or display 306 of initialization unit 300. In some embodiments, the response signal may be received directly by data recorder 12.

Figure 3A:
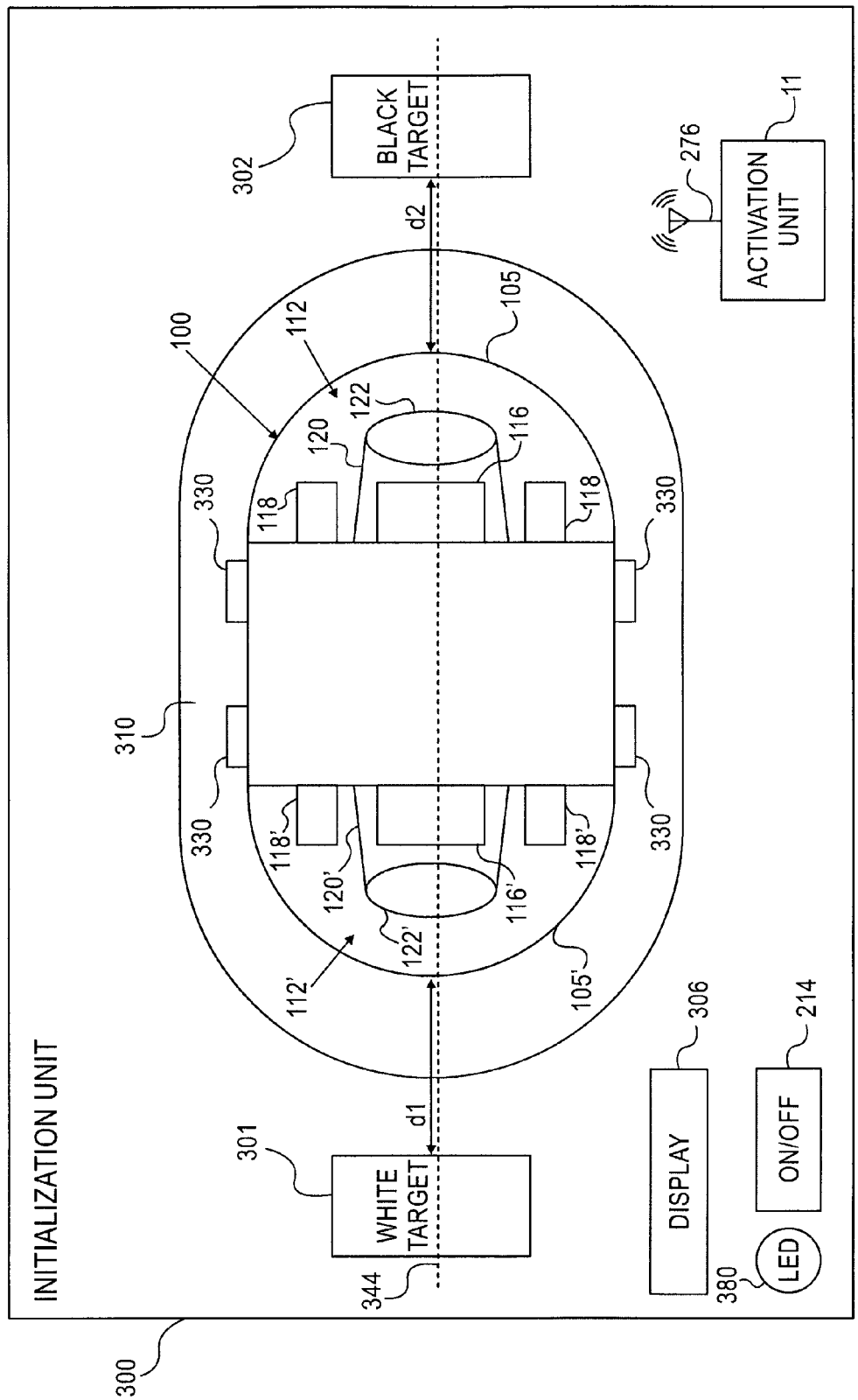
FIG. 3A, 3B are simplified diagrams of an initialization unit according to an example embodiment.
Figure 5:
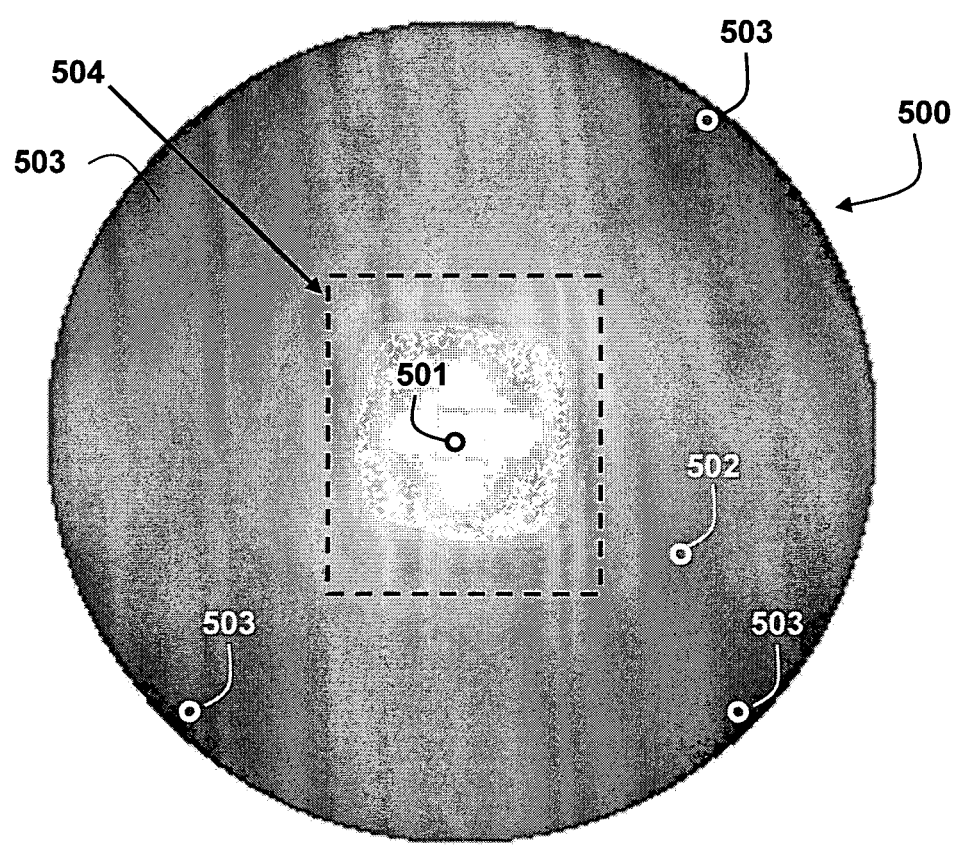
FIG. 5 shows an illumination reference map according to an example embodiment.
Figure 6A:
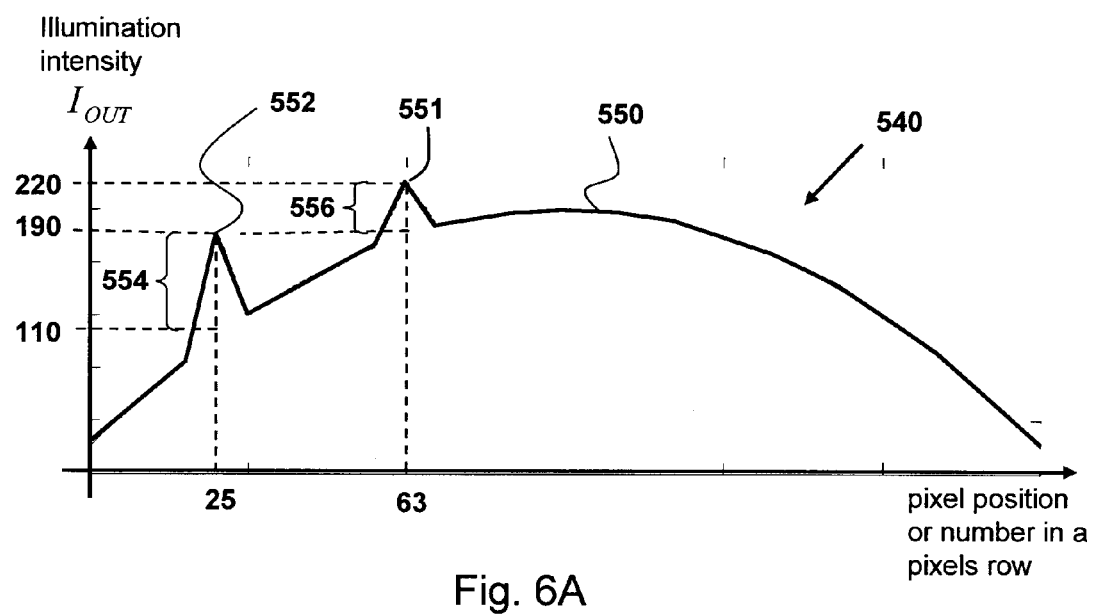
FIG. 6A shows an illumination intensity line corresponding to a line of a captured image.
Figure 7A:
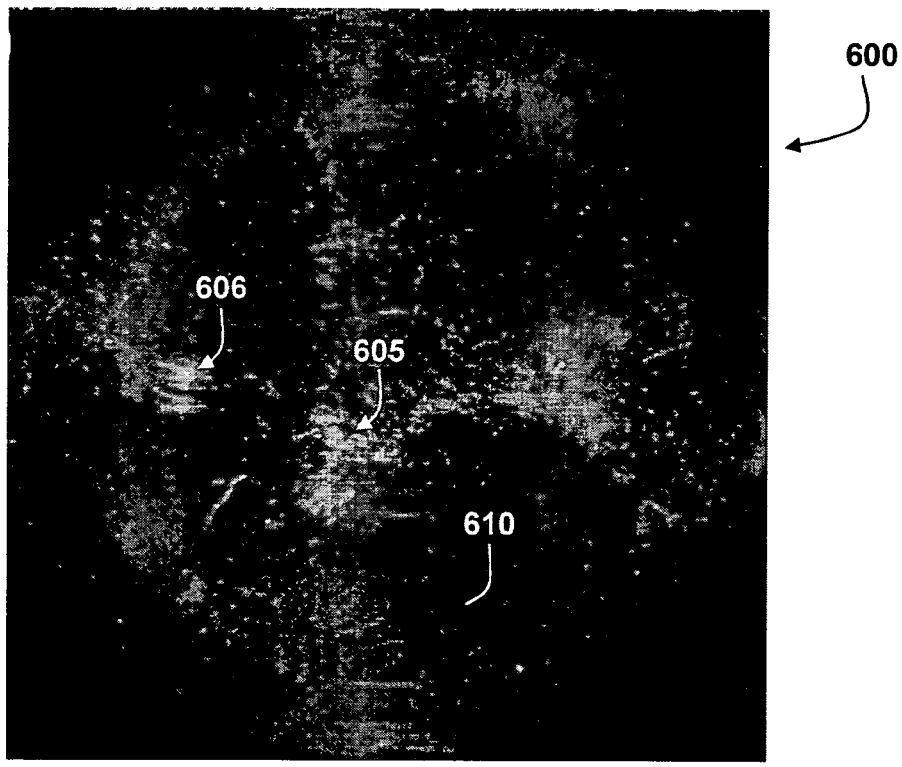
FIGS. 7A and 7B depict two optical artifact maps according to an embodiment of the present invention.
Figure 7B:
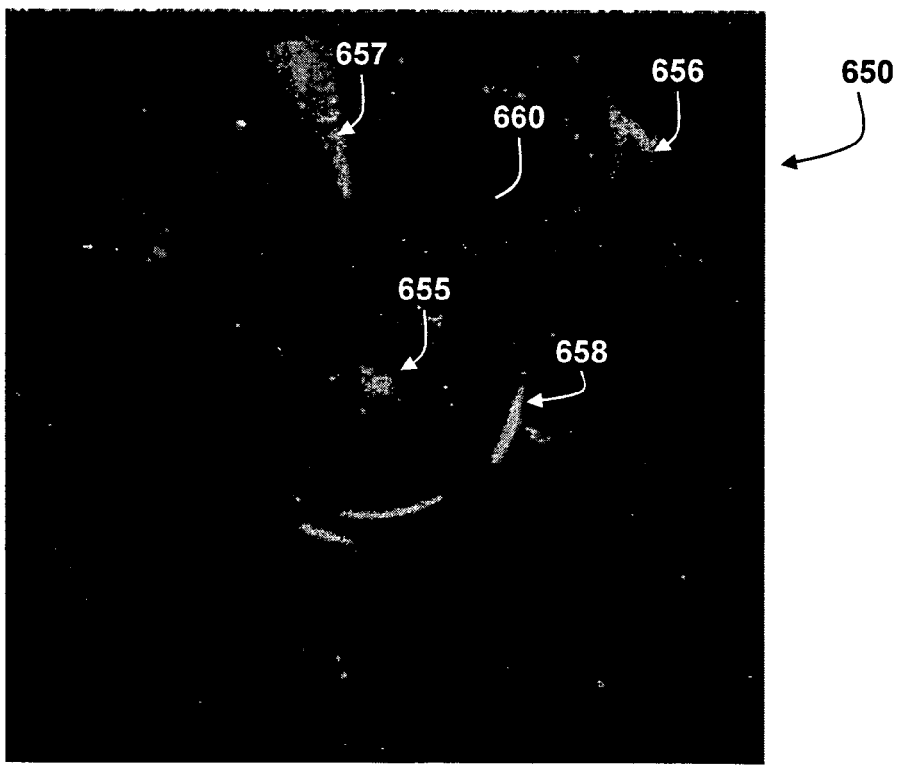

Reference is now made to FIG. 3A showing a simplified diagram of an initialization unit 300 according to an embodiment of the present invention. Engineering tolerances associated with the manufacturing of electronic and optical components of imaging devices oftentimes result in three phenomena: (1) some LEDs emit/produce more light than others under the same electrical conditions; (2) some imaging pixels are more sensitive to light (e.g., output a larger signal) than others, and (3) internal light reflections, and maybe other kinds of stray light, superimpose optical artifact on captured images. In addition, the optical window through which the in-vivo device may capture images may have flaws (e.g., scratches, distortions, etc.), and the field of view ahead of the imager may not be illuminated evenly. These phenomena, and methods for reducing their detrimental effect, are discussed below. Initialization unit 300 may enable evaluation of the field of illumination (FOI) produced by illumination units 118 and/or 118', as received by imagers 116 and/or 116', respectively, of imaging device 100 (exemplary FOI and a related intensity line are shown in FIGS. 5 and 6A, respectively). Initialization unit 300 may allow mapping of optical artifacts, which may be present in optical systems comprising imaging system 112 and/or 112' and illumination units 118 and/or 118' of imaging device 100 (example artifacts are shown in FIGS. 7A and 7B), for example by providing reference images (which are also referred to herein as "reference targets") that may be imaged by in-vivo device 100 as/for reference. Transmission and/or reception capabilities of in-vivo device 100 may be evaluated, for example by transmitting a preset signal to in-vivo device 100 and receiving the preset signal in initialization unit 300 or in data recorder 12. Initialization unit 300 may provide a power source status of in-vivo device 100, for example upon activation of in-vivo device 100 or upon a triggering event initiated by a controller, for example by a controller of initialization unit 300 or in-vivo device 100. Other testing and initialization capabilities may be embedded in initialization unit 300.

Initialization unit 300 may be shaped substantially as a box or case to accommodate or host in-vivo device 100, and may include an in-vivo device receiving space which may be shaped to snugly hold an in-vivo device 100. The in-vivo device receiving space may be implemented, for example, as a recess or concave space (e.g., concave space 310) or as a closed (e.g., light-tight) chamber. Concave space 310, an example in-vivo device receiving space, may include one or more holding, or "embracing", elements 330 which may hold, or embrace, device 100, substantially such that it does not move while positioned in initialization unit 300, for example as described in FIGS. 7A and 7B of U.S. patent application Ser. No. 12/473,064 filed on May 27, 2009 and assigned to the common assignee of the present application and incorporated herein by reference. Imaging device 100 may be held, for example, between two arms that may embrace imaging device 100, for example substantially around its housing, and secure its position in initialization unit 300 without obstructing the field(s) of view of imaging device 100. Initialization unit 300 may include activation unit 11 for operating (e.g., activating and/or deactivating) in-vivo device 100. In-vivo device 100 may be inserted into a designated concave space 310, or into a dark chamber, prior to activation. One or more reference targets 301 and/or 302 may be positioned within a field of view ("FOV") of the pertinent imaging systems 112, 112' of device 100, and may be imaged upon activation of in-vivo device 100. One (or more than one) reference target 301 may be or include, for example, a white sheet or white board to facilitate white balance calibration of the imaging unit/s of imaging device 100, for example as described with respect to FIG. 4 of U.S. Pat. No. 7,295,226 which is incorporated herein by reference. Distance d1, which is the distance between white target 301 and imaging system 112' of device 100, may be predetermined. For example, in some embodiments the optimal focus distance d1 may be equal to 10 millimeters (mm). The value of d1 may change contingent on the specifics of the optical system of the imaging device.

Initialization unit 300 may include activation switch 214 (which may be part of activation unit 11, for example), to send a wake-up signal or a shut-down signal to in-vivo device 100 while in-vivo device 100 is positioned within concave space 310 of initialization unit 300. Upon activation of in-vivo device 100, in-vivo device 100 may wake up from a dormant state and start capturing images. Since in-vivo device 100 may capture the first images while it resides in concave space 310, a white reference target, e.g., white target 301, (and/or a black reference, e.g., black target 302) may be imaged by imaging system 112' (and/or 112). White reference RGB images (and/or RGB black reference images) may be captured by in-vivo device 100 and thereafter or concurrently transmitted to initialization unit 300 or to data recorder 12. The white reference image, e.g., white target 301, may facilitate white balance or color calibration of the specific imaging system (e.g., 112 or 112'), for example by correcting the color values, for example of an RGB imager, according to intensity values of image pixels that make up the white reference image. White target 301 may also be used to produce an illumination reference map corresponding to or representing the light that is output from illumination units 118 of in-vivo device 100. In some embodiments, illumination units 118 and 118' may be tested to verify proper operation, for example by analyzing the captured image of white target 301 to validate that all illumination units operate according to an illumination scheme that is derived from a predetermined illumination map. As explained above, the illumination produced by illumination units 118 and/or 118' may be non-uniform, e.g. some areas may receive more light than others, thus creating an uneven field of illumination (FOI) that is manifested in captured images. Based on a white reference image (e.g., reference target 301), the intensity level of each pixel may be measured individually, and an illumination map corresponding to, or representing, the measured intensity levels may be stored and used later as reference, thus the name "illumination reference map". The illumination intensity of images in an image stream may individually be corrected, optimized, normalized, etc., by using the illumination reference map in order, for example, to equalize the illumination intensity of the images, or to equalize the intensity level across the entire images or across selected portions of the images. The illumination intensity or intensity level correction, optimization, etc., may be performed, for example, in real time; e.g., while images are being captured or immediately thereafter, or post factum; e.g., after the images are transmitted from in-vivo device 100 (e.g., to data recorder 12). The illumination intensity or intensity level correction, optimization, etc., is explained in more details below.

Stray light, such as light internally reflected from domes 105 and 105' of device 100 to the imagers, may degrade the quality of captured images. Stray light may be caused, for example, due to imprecise alignment of imaging system 112, dirt, scratches or due to mechanical inaccuracies caused in the production process of the dome or the assembly process of the in vivo capsule. Stray light may result in optical artifacts. However, by mapping the optical artifacts of the optical system of the imaging device, in advance, production and assembly constraints may be made less stringent because such mapping enables taking corrective measures post factum to minimize the effect of artifact. Initialization unit 300 may include one or more optical artifact reference targets, shown as black target 302. Black target 302 may be used to map optical artifacts caused by the imaging device's imaging system 112. Distance d2, which is the distance between imaging system 112 and black target 302, may be relatively large, for example 10 centimeters (cm) to 15 cm, to facilitate optimal capturing of the optical artifacts.

An image processing algorithm that improves image quality by reducing the effect of reflections from dome 105 (e.g., artifacts in the image) caused, for example, by scratches or inaccurate assembly of optical components, is described below. In some embodiments, the reflections from dome 105 may be represented as a direct current ("DC") offset (a DC offset value per pixel) of the pixel values read from imager 116 and/or imager 116'. In one embodiment, subtracting the DC offset may enable to significantly reduce, or even to completely remove reflections-infected areas, or to compensate for the detrimental effect of the dome reflections and other artifacts, to receive higher quality images of the in vivo scene. In order to determine the DC offset for pixels (on individual basis; e.g., per pixel) of an imager (e.g., imager 116), an image of an optical artifact reference (e.g., an image of black target 302) is captured by that imager. An optical artifact image may be captured, as reference, upon activation of the imaging device in initialization unit 300, and transmitted, for example, to data recorder 12 and stored there in order for it to be used as an optical artifact map. In other embodiments, the optical artifact image may be transmitted from in-vivo device 100 to receiving module 260, which may be included in activation unit 11 or initialization unit 300. Since optical artifacts may undesirably be superimposed on captured images, the detrimental effect of the artifacts can be mitigated, or even completely removed, by subtracting the optical artifact map/image from each image that is captured by in-vivo device 100. For example, the (substantially artifact-free) output image, $I_{out}(x,y)$, where x and y are 2-dimensional coordinates of the pixels, may be calculated on a pixel-by-pixel basis, by pixel wise subtracting the optical artifact map/reference, $I_{optic\_ref}(x,y)$, from the raw captured image $I_{raw}(x,y)$, as shown in formula (1):

$$I_{out}(x,y)=I_{raw}(x,y)-I_{optic\_ref}(x,y) \quad (1)$$

The resulting image $I_{out}(x,y)$ may be substantially free of optical artifacts caused, for example, by scratches, assembly and production imperfections and/or dome reflections because the subtraction operation of formula (1) cancels out the artifacts from the raw image $I_{raw}(x,y)$. In some embodiments, the subtraction of the optical artifact reference image from the raw captured image may be performed after normalizing the optical artifact reference image to the actual gain level and light pulse duration (e.g. exposure time or illumination duration) used to capture each image, for example by using formula (2):

$$I_{out}(x, y) = I_{raw}(x, y) - \frac{G_{raw} \cdot E_{raw}}{G_{optic\_ref} \cdot E_{optic\_ref}} I_{optic\_ref}(x, y) \quad (2)$$

where $G_{raw}$ is the analog gain level used to capture the (raw) image, $E_{raw}$ is the light pulse width used to capture the (raw) image, $G_{optic\_ref}$ is the analog gain level used to capture the optical artifact reference image (e.g., optical artifact); and $E_{optic\_ref}$ is the light pulse width used to capture the optical artifact reference image.

Data indicative of the actual gain level and light pulse duration used in the process of capturing each image, may be included in the telemetry data/information which may be transmitted from device 100, for example along with each image or for groups of images. Exemplary optical artifact reference images are shown in FIGS. 7A and 7B and are explained in more details below.

In order to facilitate obtaining an optical artifact reference image for 'cleaning' captured images from artifacts (e.g., reducing or removing the artifacts from captured images), initialization unit 300 may include, for example, a lid or cover for light-sealing in-vivo device 100 in concave space 310 of initialization unit 300. It may be important to seal initialization unit 300 tightly or hermetically, such that substantially no external light (light originating from outside of initialization unit 300) can reach in-vivo device 100 and/or black target 302, in order to maintain high accuracy of the optical artifact reference image (and/or the illumination reference map); i.e., in order to ensure that an image taken under these conditions is solely attributed to, or reflects, the artifacts. The optical artifact reference images (map) and/or illumination intensity reference images, which may be regarded as "initialization images", may be transmitted first or among the first images transmitted by in-vivo device 100 and recorded in data recorder 12. Therefore, initialization images may be used to process 'regular' images (e.g., images captured in the GI system) that are transmitted later to, and recorded in, data recorder 12, for example in real time. For example, as soon as data recorder 12 receives a regular image from in-vivo device 100, an optical artifact reference image, which was transferred to the data recorder earlier, may be subtracted from the regular image, for example after normalizing the optical artifact reference image, for example, according to telemetry data including or representing light gain and/or exposure time that was used to capture the regular image. In some embodiments, the corrected (improved, or enhanced) image may be stored in the data recorder 12, while in other embodiments the original image received from device 100 may be stored and the artifact removal may be performed later (for example, during subsequent processing of the image stream). This may enable faster processing of the captured image stream. In other embodiments, the subtraction of the optical artifact reference image may be performed offline, for example after the image stream is downloaded to workstation 14 and processed, compiled and/or summarized.

A status LED 380 may indicate the operating status of in-vivo device 100. For example, a green light may indicate that device 100 is operationally active, which is one of the available image capturing modes. A red light may indicate that device 100 is dormant. Other suitable indications may be used, e.g. a message may be displayed on display 306 which may be connected to or integrated into activation unit 11 and/or to/into initialization unit 300.

Figure 3B:
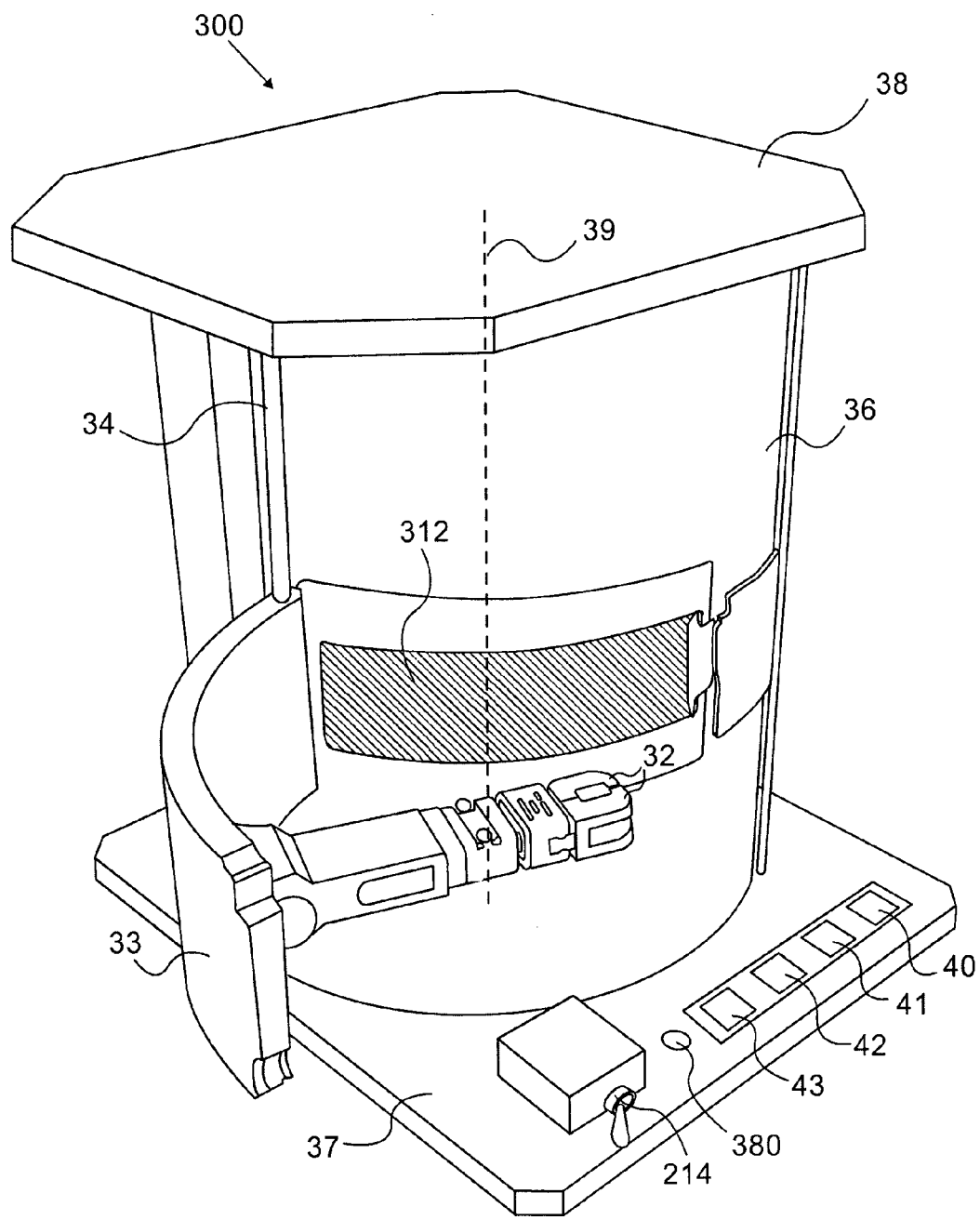

Reference is now made to FIG. 3B, which illustrates an initialization unit 300 according to an embodiment of the present invention. Initialization unit 300 may be generally shaped, for example, substantially as a cylinder 36, and it may include a base cover 37 and a top cover 38. Concave space 310 may be an inner space defined by the cylinder wall 36, top 38 and base 37. Other shapes of the initialization unit (e.g., box, sphere, ellipsoid, etc.) may be used. Antenna 276 of activation unit 11 may be embedded into the cylinder wall 36, or may be coiled around it externally or internally (e.g., inside concave space 310). For example, antenna 276 may be coiled such that its central axis is aligned with longitudinal axis 39 of the cylinder 36.

Prior to starting the initialization process (e.g., by using initialization unit 300), in-vivo device 100 is positioned substantially between holding, or capsule embracing, elements 32, which may be connected, for example, to a door 33. Door 33 (which is shown in FIG. 3B in an open state) may be opened and closed manually, or by using a door opening/closing switch, for example switch 40. Door 33 may be opened and closed by pivoting around hinge 34. In the "closed" state, door 33 may substantially seal inner space 310 and thus protect the imaging device from external light. When door 33 is closed, in-vivo device 100 may be positioned substantially in the center of inner space 310 (e.g., along axis 39 of cylinder 36), and may be situated for example at distance d1 from top cover 38 and at distance d2 from base cover 37, for example as per "d1" and "d2" of FIG. 3A. In-vivo device 100 may be secured to embracing/holding elements 32, for example, by being gripped by embracing/holding elements 32, such that optical system 112 is directed toward, or faces, top cover 38 and the other device's optical system (e.g., optical system 112') is directed toward, or face, base cover 37. In such positioning, central axis of, for example, a coil which may be used as antenna 135 of device 100 may be aligned with the central axis of antenna 276. Other alignments may be used, and in some embodiments, no specific alignment of antenna 135 and antenna 276 may be required. In some embodiments, top cover 38 may include white target 301, and base cover 37 may include black target 302, such that in-vivo device 100 may capture a white reference image (the image of white target 301 that can be used as the white reference) by using imaging system 112, and a black reference image (the image of black target 302 that can be used as reference) by using imaging system 112'. In other embodiments, both targets may be of the same type, e.g. both top cover 38 and base cover 37 may include targets 301 (or targets 302), and yet in other embodiments the targets may be interchangeable: for example by using a switch 43, a desired reference target may be selected. Other types of user interface may be used instead of, or in addition to, the switches of FIG. 3B. One or more switches which may be positioned, for example, on base cover 37 or on another outer section of initialization unit 300, may include "on/off" activation switch 214 to send a wake-up signal or a shut-down signal to in-vivo device 100 when it is positioned inside unit 300 (e.g. with door 33 closed). Other switches may include switch 40 to close/open door 33, switch 41 to transmit a command to device 100 to capture a first reference target, switch 42 to transmit a command to device 100 to capture a second reference target, and a status LED 380, for example, to indicate the operational status of device 100 or the current step, stage, or phase of the initialization process. A "phase" may be defined as having a certain group of individual steps.

Figure 4:
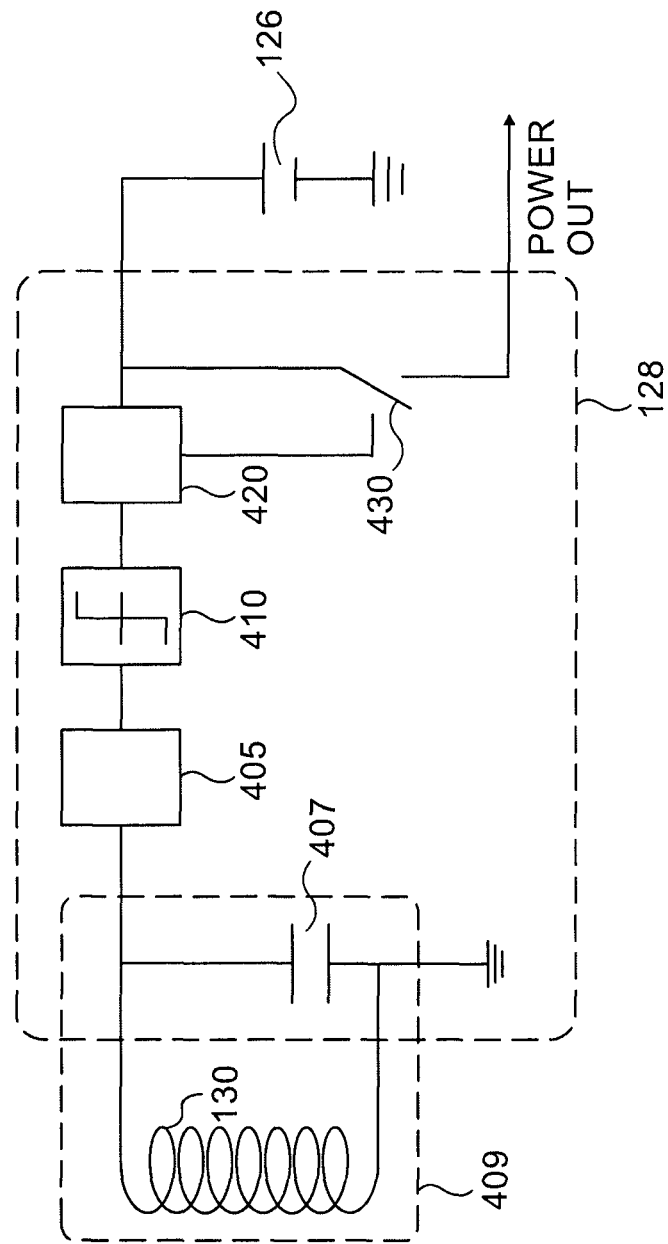
FIG. 4 is an exemplary circuit diagram of an RF switch within an in-vivo device according to an example embodiment.

Reference is now made to FIG. 4 showing an exemplary circuit diagram of an RF switch within an in-vivo device according to an embodiment of the present invention. Other suitable switches or devices receiving RF energy and acting as a switch or controller may be used. Energy radiated by antenna 276 may induce energy across Rx antenna 135 of device 100 which may trigger RF switch 128 to, for example, change the power state of device 100. According to one embodiment of the present invention, a rectifying circuit 405, for example an AC to DC converter, may be implemented to rectify the signal received, for example, by using a diode bridge and a capacitor.

Threshold block 410 may perform thresholding so that only signals above a defined threshold may initiate activation of device 100. For example, a signal above a (pre)defined threshold may signal to controller 420 to activate switch 430 to, for example, power (e.g. by using power source 126), and/or activate transceiver 127. Other components may be powered with switch 128. In one example, a signal of amplitude 1 volt may be required to pass threshold block 410. Other amplitude levels may be used. Controller 420, rectifying circuit 405, threshold block 410 or other components or their functionalities, may be included within, for example, transceiver 127.

According to one embodiment of the present invention, the RF signal generated by activation unit 11 may generate an electromagnetic field density in the range between 1 microWB/m$^2$ and 100 microWB/m$^2$. Other ranges of electromagnetic fields may be generated. In other embodiments of the present invention, in order to avoid false activation and/or deactivation of device 100, a pre-defined number of pulses or some pattern of a signal may have to pass a threshold level set by or through threshold block 410 before the device (e.g., switch 430) changes its operating state. In one embodiment of the present invention, controller 420 may include a timer and counters as well as other components or circuitries. A timer may, for example, be used to measure time intervals between pulses that may pass threshold 410. Counters may be used to count the number of pulses. For example, in order to activate device 100, four pulses may be required to pass the threshold 410 and the time interval between a pair of the pulses that pass the threshold 410 may be required to be within a certain time range, e.g. 0.1 to 10 msec. Other numbers of pulses may be used. According to one embodiment of the present invention, one or more timers may be activated only after a first pulse may have passed the threshold 410 hence saving power during a dormant state. Other methods of detecting an activation signal may be implemented.

During the dormant state of device 100, controller 420 may be powered by power source 126 so that operational activation of device 100 may be accomplished. The power consumption of controller 420 may be minimal during a dormant state, for example, between 50 to 200 nano Ampere [nA], e.g. 100 nA or 200 nA, so as to minimize depletion of power source 126 of device 100. In one example controller 420 may be only partially activated during a dormant state to facilitate minimal power consumption.

In an alternate embodiment of the present invention; RF switch 128 may be a toggle switch that may deactivate device 100 in a similar manner used to activate device 100. For example, a first pulse and/or a set of pulses may activate device 100 and subsequent pulse or a set of pulses may serve to deactivate device 100. In another embodiment a first pattern of pulses may be used and/or required to activate device 100 and a second pattern of pulses may be used and/or required to deactivate device 100. Other methods of altering the power state of device 100, e.g. activating and/or deactivation device 100 may be implemented.

In some embodiments, RF switch 128 may be toggled into a fixed or permanently closed position such that RF switch 128 may retain a closed position or 'on state' even after the RF field created by the external activation unit 11 may have ceased and/or terminated.

In operation, device 100 may be manufactured, packaged, or distributed with RF switch 128 in an open position such that some or all of power from, for example power source 126, is not supplied to the electrical components (e.g. illumination source 118, transceiver 127, imager 116, etc.) of device 100, and so that one or more functions of device 100, e.g. the imager function, is dormant or not operative. At a desired time, for example when device 100 is to be tested or before device 100 is to be ingested by a patient or user, antenna 135 may be exposed to radio frequency radiation generated by external activation unit 11 while device 100 is still outside a body, or ex-vivo. As a result of the induced voltage on antenna 130, RF switch 128 may toggle into a closed position. The circuitry of device 100 may allow power from a power source, for example power source 126, to power one or more electrical components of device 100.

In some embodiments, a further exposure of antenna 130 to a pre-defined RF radiation pattern may toggle RF switch 128 to an open position, thereby shutting off a power supply of device 100 and de-activating one or more functions and/or electrical components of device 100. In some embodiments, the activation and deactivation capability of device 100 may be used during testing device 100, such as for example factory testing prior to shipment. Activation and deactivation of device 100 may be performed repeatedly as required.

Reference is made to FIG. 5, showing an exemplary illumination reference map 500 according to an embodiment of the present invention. Illumination reference map 500 may be captured, for example, by in vivo device 100 upon activation of device 100, for example, in initialization unit 300. Illumination reference map 500 may be captured using a white target (e.g., white target 301), or a different target which preferably may be of a white or other light color. Illumination reference map 500 demonstrates a non-uniform illumination profile of illumination units 118, 118' of in-vivo device 100. The resulting illumination level across the illumination profile may vary from one pixel to another according, for example, to the location of the one or more illumination units 118, 118' relative to the respective pixel in imagers 116, 116', due to non-uniformity of illumination units 118 (as per the permissible engineering tolerances explained above), and due to the different light paths traversed by the reflected light. In some embodiments, it may be beneficial to obtain a uniform or substantially uniform, or otherwise optimal, illumination reference map, for example since using uniform illumination generally improves the quality of the images captured by device 100. For example, if the whole image captured by in-vivo device 100 is uniformly illuminated, it may be easier to detect pathologies in the images, or the images may be easier to view in a higher frame display rate since the objects in the images may be clearer, or relatively accurate 'device-to-object' distance measurements may be carried out, etc. Illumination reference map 500 may include different visually-distinct illumination intensity areas. For example the area around point 501 (e.g., area 504) is relatively bright due to a large amount of light reaching the central area of the image and/or due to the respective pixels of the imager being more sensitive to light than other pixels. The pixels around and near point 502 have lower illumination intensity levels, as demonstrated by the relatively darker pixels around point 502. Areas in the vicinity of points 503 (for example) receive very little illumination and/or are less sensitive to light, and therefore they appear as darker areas in illumination reference map 500. Illumination reference map 500 may be captured upon activation of in-vivo device 100, and thereafter stored, for example, in data recorder 12. Illumination reference map 500 may then be used, for example by data recorder 12 or by workstation 14, to correct or rectify images after they are received and/or stored. In one example, the illumination correction process may be performed on the fly, e.g. each captured image may be corrected before it is transmitted to data recorder 12. The illumination-corrected images, which are referred to herein also as "corrected images" or "enhanced images", may then be stored, for example, in data recorder 12. In other embodiments, the illumination correction process may be performed offline, after the images are recorded, for example in data recorder 12, or after the images are downloaded to workstation 14. In some embodiments, a predetermined illumination reference map may be determined in advance (e.g., during manufacturing), and illumination reference map 500 may be compared to the predetermined illumination map to determine corrective adjustment and operation of the illumination sources. A predetermined illumination reference map may be stored, for example, in data recorder 12 or in initialization unit 300. For example, if the difference between the predetermined illumination reference map and illumination reference map 500 is larger than a predefined threshold value, for example more than 10% difference in the illumination reference level for a single pixel or for a predetermined number, group, or subset of pixels, the illumination source may be determined to be or regarded defective and the functionality test may report to the user a failure of the illumination test, or may report or issue a general capsule activation failure signal. The difference between the predetermined illumination reference map and illumination reference map 500 may be calculated on a pixel-by-pixel basis; e.g., by pixel wise subtracting illumination reference map 500 from the predetermined illumination reference map.

FIG. 6A shows an example illumination intensity graph 540 of a line of pixels corresponding to a captured image, according to an embodiment of the present invention. The Y-axis of graph 540 denotes the pixels' intensity level, or pixels' output $I_{OUT}$, and indicates the grayness level along a particular pixel line. The X-axis of graph 540 denotes the relative location of pixels along the pixel line for which illumination intensity line 550 has been measured. The relative locations of pixels along the X-axis may be measured in millimeters or in other length units. Alternatively, pixels along a pixel line may be numbered (e.g., pixel #1, pixel #2, and so on). For example, the intensity level of pixel #25 is 190. Intensity lines similar to illumination intensity line 550 may likewise be measured, drawn or devised for other pixel lines that make up the imager's array of pixels.

As an imager of an in-vivo device includes an array of rows, or lines, of pixels, each intensity line derived from such a pixel line may be thought of as a "cross section" of a captured image at that line of pixels. Illumination intensity line 550, which is an example cross section of an image, includes two conspicuous aberrant or irregular peaks (e.g., visual information) 551 and 552. Due to the non-linearity, or non-uniformity, of the field of illumination (FOI), the apex of peak 552 is lower than the apex of peal 551 (190 versus 220, as shown in graph 540) even though peak 552 protrudes more than peak 551 relative to the respective 'background' (i.e., relative to line 550)—peak 552 has a height of about 80, as shown at 554, whereas peak 551 has a height of about 30, as shown at 556. The non-uniform FOI, which is expressed in FIG. 6A as a curvature of illumination intensity line 550, makes it difficult to detect and/or extract visual information in/from images, or to interpret visual information correctly. One way to overcome problems caused by non-uniform FOI is described below in connection with FIG. 6B and FIG. 6C.

Figure 6B:
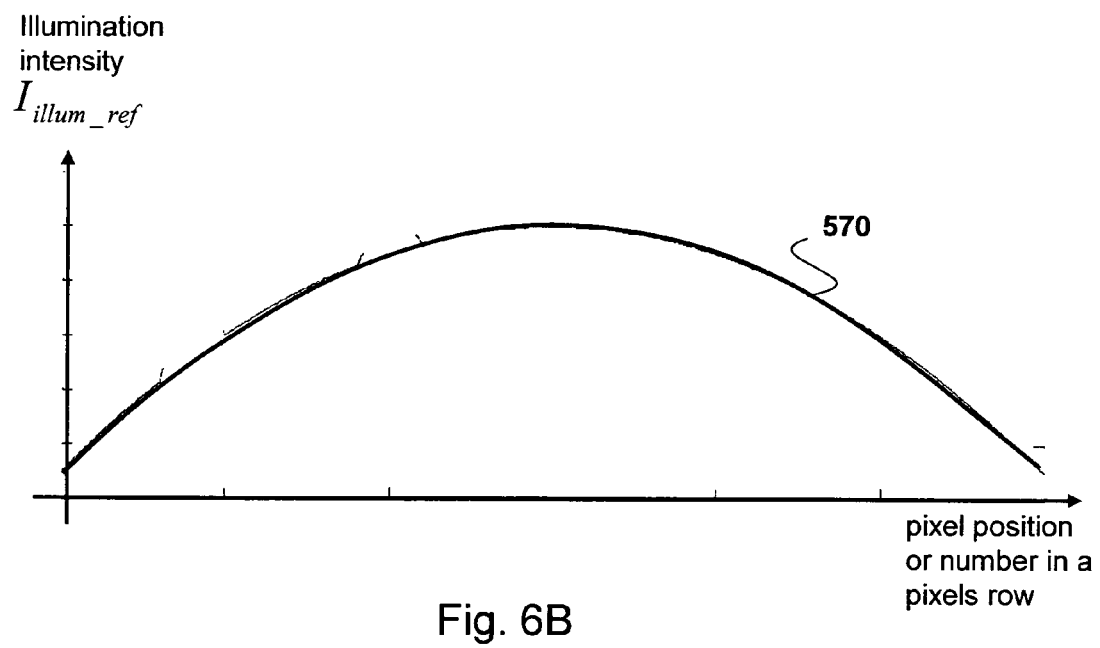
FIG. 6B shows an illumination intensity line corresponding to a line of an image of a white target according to an example embodiment.

FIG. 6B shows an example illumination intensity line 570 corresponding to an example line of pixels in a pixels' array used to capture a white target. Illumination intensity line 570, which is an example illumination reference line, and other similar illumination reference lines which are not shown in FIG. 6B, make up an illumination reference map, denoted by $I_{illum\_ref}$. The illumination reference line 570, as well as the entire illumination reference map of which illumination reference line 570 is part, is obtained by using initialization unit 300. The detrimental effect of the non-uniform FOI, as demonstrated in FIG. 6A, may be mitigated or removed by using illumination reference lines such as illumination reference line 570, as demonstrated in FIG. 6C, which is described below.

Figure 6C:
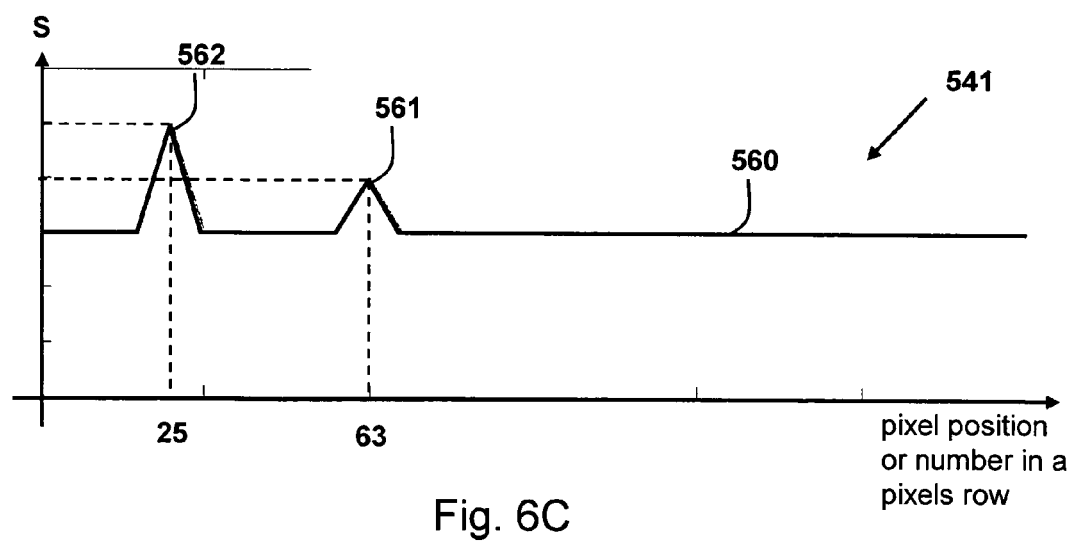
FIG. 6C shows a scene reflectance, S, graph according to an example embodiment.

FIG. 6C shows a 'scene reflectance' (S) illumination intensity graph 541 corresponding to a normalized ratio between the illumination reference line 570 of FIG. 6B and the illumination intensity line 550 of FIG. 6A, according to an embodiment of the present invention. A scene reflectance, S, may be defined as a function of a normalized ratio between an output image $I_{OUT}$ (e.g., a captured image) and an illumination reference map $I_{illum\_ref}$, which is obtained, for example, by using a white target as a reference image. S may be calculated, for example, by using formula (3):

$$S = a \cdot \frac{I_{out}(x, y)}{I_{illum\_ref}(x, y)} + b \quad (3)$$

where (x,y) denote coordinates of pixels in a 2-dimensional pixel array, a and b denote constants that may be predetermined, for example, based on the number, N, of binary bits used to quantize the scene reflectance output of the pixels. For example, if N=8 bits, then the scene reflectance output of each pixel can have a value between 0 and 255, where '0' and '255' may, respectively, represent zero intensity and maximum intensity. In general, the scene reflectance (S) can have a number between 0 and $2^N-1$, and constants a and b may be derived from, or be contingent on, N. Theoretically, if lines 570 and 550 were identical, then line 560 would have been a straight line. However, line 550 includes image peaks 51 and 552 which are missing from line 570, and using line 550 as is would have made the identification of peaks 551 and 552 difficult due to the non-uniformity of the illumination, as discussed above. However, using formula (3) removes, neutralizes, or mitigates the adverse effect of the non-uniform illumination, and thus makes visual details/information in images more discernible/conspicuous and, therefore, more easily detectable.

After applying formula (3) to illumination line 550 of FIG. 6A and to illumination line 570 of FIG. 6B, the apex of peak 552 is higher then the apex of peak 551 (the apex of peak 552 is shown at 562 and the apex of peak 551 is shown at 561). Using formula (3), therefore, emphasize image details in regular images, and puts each such detail in the correct proportion not only relative to its immediate background, but also relative to the other details in the image.

Reference is now made to FIGS. 7A and 7B, depicting two exemplary optical artifact maps according to an embodiment of the present invention. An optical artifact map 600 of FIG. 7A or an optical artifact map 650 of FIG. 7B, for example, depict an image captured by an in-vivo device 100, which may have a relatively rough dome 105. Optical artifact map 600 or 650 may be obtained by device 100, for example by capturing an image of a black target, e.g. black target 302. In an optimal production and assembly of device 100, the optical artifact map may be produced by capturing an image of a completely black target. In such cases, it may be determined that there are no visible artifacts in the captured images and, in such cases; the entire area of the captured image would be black. However, as described above, devices such as device 100 are prone to scratches, optical imperfections due to manufacturing tolerances, undesired reflections, etc. Therefore optical artifact map 600 or optical artifact map 650 may include black areas such as area 610 in FIG. 7A and/or area 660 in FIG. 7B) as well as several regions with, or 'infected' by, artifacts such as spots, lines or areas with a certain, 'non-black', level of illumination for pixels in these regions. Areas 605, 606, 655, 656, 657 and areas 658 in FIG. 7A and FIG. 7B, respectively, are example of artifact-infected areas; that is, these areas are undesirable bright due to artifacts. Artifact-infected areas may reduce quality of images captured by device 100. By compensating for these artifacts, for example, by using optical artifact map 600 (e.g., subtracting the optical artifact map of device 100 from each captured image), an image stream of improved quality may be produced, in which images are substantially free of artifacts or the amount of artifact is reduced to an acceptable or ignorable level. The elimination (or significant reduction) of the artifacts may be performed, for example, in data recorder 12, before or after the images are stored in data recorder 12. That is, an image received at data recorder 12 can undergo the artifact-elimination process and the consequent artifact-free image may be stored in data recorder 12, or the received image may first be stored and then processed to remove the optical artifact contained therein. Alternatively, the elimination (or significant reduction) of the optical artifacts may be performed in workstation 14, for example after the image stream, or part of the image stream, is transferred from data recorder 12 to workstation 14.

Figure 8:
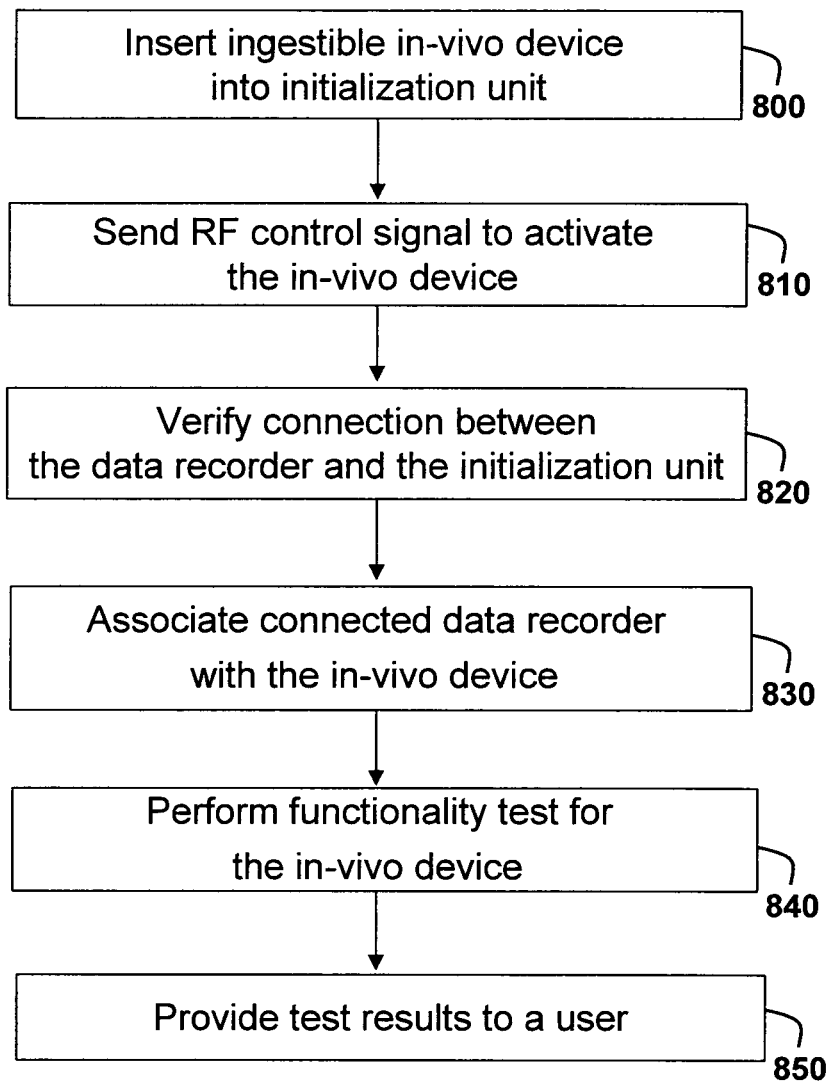
FIG. 8 is a flow chart describing a method of activating, initializing and testing an in vivo device according to an embodiment of the present invention.

Reference is now made to FIG. 8, a flow chart of a method of activating an ingestible in-vivo device, such as in-vivo device 100, in accordance with an example embodiment of the invention. In block 800, an initialization unit (e.g., initialization unit 300 of FIG. 3A or FIG. 3B) may host or accommodate in-vivo device 100 for activating, calibrating, testing, etc., the in-vivo device. The in-vivo device may be positioned in a predetermined place in the initialization unit for performing these processes. For example, the in-vivo device may be placed in concave space 310 and/or be secured inside the initialization unit by using protruding elements 330, such that the in-vivo device is aligned to optical axis 344, along which white target 301 and black target 302 may be positioned. In block 810, activation unit 11, which may operationally be part of initialization unit 300, may activate in-vivo device 100 by transmitting an activation RF signal, also referred to herein as "RF control signal". In some embodiments, transmission of the RF signal to in-vivo device 100 may be implemented by inserting in-vivo device 100 into, for example, a space that is substantially circumscribed, surrounded or encircled by antenna 276. Antenna 276 may be configured to facilitate generation of an RF electromagnetic field that is strong enough to control the operation of RF switch 128, for example to switch it on and off. In some embodiments, placing in-vivo device 100 in the initialization unit may be performed prior to the ingestion or insertion of the in-vivo device into an in-vivo area. In some embodiments the power of the RF signal irradiated from antenna 276 and/or the frequency of the RF signal may be pre-determined. In some embodiments, the predetermined power of the RF signal irradiated from antenna 276 may be set such that a magnetic flux density between 1 micro Weber per square meter (micro Wb/m^2) and 100 micro Wb/m2 be generated for a predetermined time period. For example, the power of the RF signal irradiated from antenna 276 may be set such that a magnetic flux density of 1.5 micro Wb/m2 is generated for a period of several seconds.

An activation command to generate the RF control signal may be sent from a controller, for example from internal controller 212 of activation unit 11. Controller 212 may be connected to a user-operable interface unit such as an "ON/OFF" switch 214, which may optionally be an integral part of activation unit 11. In some embodiments, an activation command to generate the RF control signal may be sent to antenna 276 from data recorder 12, for example via connection 180. For example, the activation command may be issued by, or originate from, a controller residing in data recorder 12, which may be connected to the activation unit 11 in initialization unit 300. The activation command may be received by control unit 212 of activation unit 11. Energy conveyed by the RF signal generated by activation unit 11 may induce energy in a component within the in-vivo device 100. If the induced energy is sufficiently high, a switch contained in the imaging device may be activated, deactivated or toggled so as to change its state, for example, from "on" to "off" or from "off" to "on". The RF control signal may be devised such that it has a unique control pattern, or control code, for each available state of the in-vivo device. In one embodiment of the present invention an RF control signal to wake up imaging device 100, or to turn on components in device 100 on selective basis may be predefined, for example it may include a predefined series or pattern of RF pulses; an RF control signal to shut down device 100, or to turn off components in device 100, may include a different predefined series or pattern, e.g. a second predefined series or pattern of RF pulses. In one example, the RF control signal used to turn off device 100 or selected components thereof (i.e., an "off" RF control signal) may be relatively short; e.g., it may include a short burst or series of pulses. An "on" RF control signal, which may be used, for example, to turn on device 100 or to wake up device 100, may be longer than the burst or series of pulses associated with the "off" state. In other embodiments, different predefined patterns of RF control signals may be used to control the operation of in-vivo device 100. Upon receiving the RF control signal, power from power source 126 may selectively be provided to one or more electrical components of imaging device 100 through a turned "on" switch within the in-vivo device. In some embodiments, activation of switch 430 of FIG. 4 may close a circuit that may power one or more electrical components (e.g. transceiver 127, illumination source 118, imager 116, or other components). In some embodiments, switch 430 may retain its 'closed' state so that power may continue to be provided from power source 126 to a component of the device 100 even in the absence of RF radiation. Other methods for remotely activating an in-vivo device with the use of RF control signals may be implemented.

In block 820, proper functional connection, for example via connection 180, between data recorder 12 and activation unit 11 and/or initialization unit 300 may optionally be ascertained. For example, upon connecting activation unit 11 to data recorder 12, activation unit 11 may report, for example by using an LCD display which may be part of activation unit 11 or data recorder 12, that the connection between these systems is operational. Ascertaining the operational connection between activation unit 11 and data recorder 12 may be based, for example, on voltage detection methods or on a handshake process, as known in the art (e.g., USB connection detection). In some embodiments, activation unit 11 may be a component of data recorder 12, for example it may be embedded in it and, in such cases, the phase of such connection ascertaining may be rendered unnecessary.

Block 830 includes associating data recorder 12, which is connected to activation unit 11, to in-vivo device 100. In one embodiment, activation unit 11 may be connected to data recorder 12 during activation of in-vivo device 100. This embodiment may enable associating the activated in-vivo device to the data recorder by using, or through, the activation unit. The user may click or depress a button that may be provided, for example, on data recorder 12 or on activation unit 11, to associate the specific in-vivo device 100 to data recorder 12. For example, data recorder 12 may receive identification signals, or other signals, from every active ingestible in-vivo devices in a specific area. A list of such devices may appear, for example upon demand, on a display unit 173 of data recorder 12. A user may select from the list of active in-vivo devices the in-vivo device that is to be associated with data recorder 12. In another embodiment, the data recorder may be initialized with a specific in-vivo device identification (ID) data or code, and in this case data recorder 12 may not need to scan the area for all active devices.

For example, in-vivo device 100 may have an 'onboard' unique identification (ID) code that may be provided during the production process. The device ID code may be stored, for example, in memory 129 of FIG. 1. The device ID code may include, for example, a numeric string of characters or an alphanumeric string of characters. The device ID code may be transmitted by in-vivo device 100 upon activation (e.g., as part of a handshake or handshake like process), and/or as part of telemetry information/data that device 100 may periodically or intermittently transmit after it is activated. While in some embodiments data recorder 12 may receive signals from any active in-vivo device within reception range, in other embodiments data recorder 12 may be allowed to receive, or to respond to, signals only from a specific in-vivo device. For example, data recorder 12 may be configured, e.g. by pressing a button or by using any other suitable user interface, to only accept and/or respond to signals that are received through connection 180 from activation unit 11. In another example, data recorder 12 may detect the connection of activation unit 11 to data recorder 12, and upon activation of device 100 data recorder 12 may automatically receive signals only through connection 180. For example, during RF activation of device 100 by activation unit 11, signals transmitted from device 100 may be received by receiving module 260 (e.g., by using antenna 277) in activation unit 11, and sent from receiving module 260 to data recorder 12, for example, via connection 180. Data recorder 12 may accept these signals, and a processor in data recorder 12 may extract the in-vivo device's ID code from a data packet received with these signals, for example from telemetry data sent by in-vivo device 100, and use it after ingestion/insertion of in-vivo device 100 in vivo. For example, only data sent from the in-vivo with a particular device ID code (e.g., data including an ID code associated with data recorder 12) may be stored in data recorder 12. In case the system is capable of two-way communication, for example in a case where control data can be sent from data recorder 12 to device 100, data recorder 12 may be programmed to transmit control data or other data only to a particular in-vivo device, e.g. to device 100, which was associated with data recorder 12 during activation of device 100. In-vivo device 100 may be programmed, for example on-the-fly, during the activation process to receive and to respond to control data that it receives only from the data recorder with which it is associated. The association between an in-vivo device and a data recorder with which it operates may be implemented, for example, by storing (e.g., by burning or writing) identification (ID) data, for example a unique serial number, of the data recorder in a memory in the in-vivo device. In some embodiments, the ID data of the data recorder may be stored in the imaging device in advance (e.g., during manufacturing, or before distribution, of the imaging device). In other embodiments, the data recorder may transfer its ID data to the in-vivo device during the first communication session between them. In some embodiments, the data recorder's serial number may be stored in the in-vivo device's memory (e.g., in memory 129) once, without permitting another data recorder to erase, overwrite or rewrite it. In another example, after device 100 is activated and associated with a specific data recorder 12, it may sometimes be useful (for example if the specific data recorder malfunctions) to associate a different data recorder with the in-vivo device, and, thus, to allow writing ID data of another data recorder into memory 129 of device 100. In some embodiments, more than one data recorder may send control data to device 100 and a specific serial number of a data recorder may not be written into the device's memory.

Once in-vivo device 100 is associated with data recorder 12, data recorder 12 may transmit, for example, control data (and/or other type of data) to in-vivo device 100. In one embodiment, if data recorder 12 transmits control data and/or other type of data and two or more in-vivo devices are activated, then more than one in-vivo device may receive the control data and/or the other type of data. The transmitted control data and/or other type of data may include the in-vivo device's ID code. In one example, device 100 may receive, from the data recorder, an ID code embedded in control data, and compare the received ID code to its own unique ID code: in one embodiment, device 100 may respond to the control data (or other type of data) it receives from the data recorder only if there is a match between the ID code it receives from the data recorder and its own ID code. In other embodiments, device 100 may respond to control data and/or to other type of data regardless of which data recorder transmitted the data. In some embodiments, it may be useful to allow an in-vivo device to respond to certain types of control data indiscriminately originated from any data recorder, and to selectively respond to other types of control data only if they are originated from a specific or associated data recorder. Other configurations are possible.

Upon activation of device 100, it may be useful to allow a user to perform one or more functionality tests (block 840) to verify correct performance of device 100 or its components, for example:

to test illumination units 118, 118' and see if they operate correctly and provide the expected field of illumination to test the power level of battery 126 in order to know if it has sufficient power for completing an in vivo imaging procedure to test imaging (or optical) systems 112, 112' to see if that area is free of scratches and defects to test the optical system in order to see if it is properly aligned to test the transmission/reception functionalities/capabilities of device 100

For example, a functionality test of the illumination source/units may include, checking or using an illumination reference map, for example by a processing device which may be included in data recorder 12, in activation unit 11, and/or in workstation 14. Data recorder 12 or activation unit 11 may receive one or more illumination reference maps which may be captured by device 100. The illumination reference map (or illumination reference images) may include for example one or more images of one or more predetermined optical targets, e.g., a white target. The illumination reference maps/images may be transmitted from ingestible device 100 to data recorder 12, and may be stored there. The illumination reference map may be compared to a predetermined illumination reference map, and a processor may determine whether the illumination units are properly functioning. The illumination reference map may be used to improve the dynamic light range of images captured by device 100, for example by processing the images and controlling (e.g., adjusting the) image gain level based on the illumination reference map.

In some embodiments, the illumination reference map may be used to calibrate illumination sources 118, or illumination sources 118', or both illumination sources of in vivo device 100. For example, the level of electric current to be provided to an illumination source may be determined, for example, by a control unit (not shown) that may reside in data recorder 12 or in workstation 14. The control unit may transfer to the in-vivo capsule a corresponding control signal to effectuate a desired change in the current provided to the pertinent illumination sources. After the desired change in the illumination source(s)'s current is effectuated by the in-vivo device, another illumination reference map may be obtained, and the process including adjustment of the illumination sources' current and obtaining the consequent illumination reference map may be reiterated until an optimal or the best illumination reference map is obtained.

In another example, a functionality test of the imaging system may include capturing an optical artifact map, for example, by using one or more imaging systems 112 and 112' of in-vivo device 100, to determine whether the imaging unit(s) is/are in a proper operational state. The optical artifact map may include, for example, one or more images of one or more predetermined targets, e.g., black target 302. In some embodiments, the optical artifact map may be analyzed to determine whether the in-vivo device's optical dome 105 is intact, or substantially undamaged. For example, the optical artifact map may be analyzed to determine the number and severity of scratches and other defects, and/or to calculate the percentage of faulty or defective areas in the field of view (FOV). In one example, the percentage of faulty/defective areas in the field of view may be calculated based on the number of pixels, in the pixels making up the optical artifact map, whose intensity values are higher than a predetermined threshold value. In another example, if a particular pixel in the optical artifact map has a value which is, for example, higher than a predetermined maximum acceptable level, the device's optical dome may be regarded as faulty or defective. Other methods of analyzing the optical artifact map may be used.

In the optical artifact map, an image of a black target or a distant target may be acquired. The activation unit may include a light-tight or lightproof chamber for hosting an imaging device (e.g., in-vivo device 100), and for preventing external light from reaching the hosted imaging unit/system, for example when the hosted in-vivo device undergoes a test procedure. For example, the internal surface of the chamber of the activation unit hosting the in-vivo device may be covered with a black optical coating material such as Magic Black™ coating material manufactured by Acktar Advanced Coatings Ltd, to ensure that most, if not all, of the photons reaching the imager originate from light emitted from an illumination source of the tested in-vivo device and reflected back from the scratches and/or other defects of the dome or other component of the imaging unit/system. The portion of light which is not reflected back from the dome may travel outside the in-vivo device and be absorbed by the optical black target. Scratches and artifacts on an imaging device's dome may likewise affect both the optical artifact map and the images captured by the in-vivo device. Therefore, by subtracting the optical artifact map (which functions as a reference artifact image) from images captured by the imager of the in-vivo device during regular GI imaging, most of the artifacts in the GI images may be removed, thus improving the quality of the images.

An artifact threshold value may be set by a user, or may be predetermined. For example, an artifact threshold value may be set to allow up to 10% impediment or obscuring of the field of view (FOV) due to optical artifacts. Based on the used artifact threshold value, a decision may be made and provided by the activation unit or data recorder to a user, regarding whether optical dome 105 qualifies for GI imaging. The optical artifact map may later be used to remove visible artifacts from captured GI images, as shown in FIGS. 7A and 7B, which are described above. The same artifact removing procedure may be used/repeated for each optical dome of the in-vivo device.

In one embodiment, for example if an in-vivo device includes two or more imaging systems (e.g., imaging systems 112 and 112'), it may be preferable to obtain an illumination reference map and an "artifact reference map" from each imaging system separately. Optical target 301 (an example white target) and optical target 302 (an example black target) may be used to obtain separate reference maps; e.g., illumination reference map and an optical artifact map. In-vivo device 100 may capture images of the one or more optical targets, for example upon activation of device 100, or immediately or shortly thereafter. For example, after activation unit 11 activates in-vivo device 100, a white target may be positioned in front of imaging system 112' (as shown at 301 in FIG. 3A) and, similarly, at the same time or at different times, in front of optical system 112. The process including usage of the white target to obtain an illumination reference map may be regarded as a first calibration (or initialization) step of imaging systems 112 and 112'. Continuing the example, a black target may be positioned in front of in-vivo system 112 (as shown at 302 in FIG. 3A) and, similarly, at the same time or at different times, in front of optical system 112'. The process including usage of the black target to obtain an artifact map may be regarded as a second calibration step. The time period during which the optical targets are used to capture the respective map (e.g., illumination reference map, optical artifact map) may be predetermined to be, for example, five seconds. Other parameters may be used (e.g., shorter or longer than five seconds). Other types and/or colors of targets may be used, for example depending on the type of in-vivo device 100 or the type of imaging procedure that is planned, or the type of the imaging system(s) used by device 100. In some embodiments, the order of use of the different optical targets; e.g., the order in which the optical targets are presented/displayed to the imaging systems 112 and 112', may not be important. Other calibration/initialization procedures or steps may be used. In other embodiments, optical targets 301 and 302 may be fixed targets, and an imaging system positioned near an optical target may use the optical target to obtain a reference map (e.g., imaging system 112 may be positioned near optical target 302 to obtain an optical artifact map, and imaging system 112' may be positioned near optical target 301 to obtain an illumination reference map as demonstrated in FIG. 3A). In order to allow each imaging system 112 and 112' to obtain both an illumination reference map and an optical artifact map, device 100 may be positioned in an initial position, in which each of the imaging systems is capturing an image of a different optical target and, then, device 100 may be rotated e 180 degrees to allow each imaging system to capture an image of the other optical target. For example, imaging device 100 may be positioned in an initial position in which imaging system 112 faces black optical target 302 and imaging system 112' faces white optical target 301, and, after each imaging system captures an image of the respective optical target, device 100 may be rotated 180 degrees to enable imaging system 112 to capture an image of white target 301, and imaging system 112' to capture an image of black target 302. Rotating in-vivo device 100 180 degrees is an example way to expose each of the device's imaging systems to both types of optical targets in order to obtain both an illumination reference map and an optical artifact map for each imaging system. For example, after obtaining a reference map of target 302 (e.g., an optical artifact map) with imaging system 112 and a reference map of target 301 (e.g., an illumination reference map) with imaging system 112', device 100 may be rotated such that imaging system 112 may face optical target 301 and imaging system 112' may face optical target 302. After device 100 is rotated, a reference map of target 302 may be obtained with, and for, imaging system 112', and a reference map of target 301 may be obtained with, and for, imaging system 112. A similar method may be used in case of one or more imaging systems. As explained herein, the different reference maps may be obtained for each imaging system by swapping the optical targets.

In one embodiment, the activation unit 11 may include a lid to substantially completely close the in vivo device inside the activation unit. Such encasing may prevent ambient or environmental light from reaching the imaging unit(s) of device 100, which is helpful when an image of an optical target is captured by an imaging system of device 100 to obtain a reference map, such as an illumination reference map or an optical artifact map.

In one embodiment, in order to test the transmission/reception functionalities of in-vivo device 100, a specific test signal may be transferred to in-vivo device 100. The test signal may be transferred to device 100 using, for example, PWM key modulator 174 of activation unit 11 and antenna 276. In another embodiment, the test signal may be transferred from data recorder 12 to device 100. The test signal may have a predetermined waveform. Device 100 may be programmed to respond to the test signal by transmitting a response signal back to the sender of the test signal (e.g., activation unit 11, data recorder 12). The response signal may be similar or identical to the test signal, or it may have other forms (e.g., waveforms). The response signal may be received for example, by receiving module 260 of activation unit 11, or by a transceiver of data recorder 12. Upon receiving an expected response signal (e.g., by activation unit 11 or data recorder 12), the quality of the transmission and reception of signals from/by device 100 may be determined. If an unexpected signal is returned, or if after a timeout period no response signal is received, it may be determined that the transmitter circuit and/or the receiver circuit of device 100 is/are defective, and an indication or message regarding the test results (e.g., "pass", "failure", etc.) may be provided to a user.

The results of the one or more functionality tests may be provided to a user (block 850). For example, activation unit 11 may include one or more indicators, such as LED indicators, to indicate the different functionalities of device 100 that are, or have been, tested, as well as the current status (e.g., test procedure is going as planned) and final status or result (e.g., test was successful or test failed) of each test. For example a red LED may indicate that a specific functionality failed the test. A green LED may indicate that one or more functionalities passed the tests. In one embodiment, the indications may be provided to a user on a display of, or associated with, data recorder 12, for example the indications may be displayed on an LCD display, for example, as a text message, and thus the LCD display may act as an indicator. In some embodiments, activation unit 11 may include display components which may indicate to a user the results of, for example, one or more functionality tests. In some embodiments, if a specific component or circuit or process of in-vivo device 100 fails one or more of the tests, activation unit 11 may automatically send a de-activation signal to the in-vivo device to switch it off.

In one embodiment, some of the steps mentioned above are optional and may be avoided. In some embodiments, the execution order of some or all the steps mentioned above may change. While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the true spirit and scope of the invention. For example, the initialization, testing and calibration processes, and, in general, each operation or process discussed herein is likewise applicable to any in-vivo device that includes one imaging system or more than one imaging system, where each imaging system may include an imager, an optical system (e.g., lens, lens holder, etc.), an illumination source, etc.

The invention claimed is:

1. A system for accommodating and initializing an in-vivo device, said in-vivo device comprising a housing, the in-vivo device housing comprising an imaging system, an illumination source, a transceiver and a radio frequency operable switch, the system comprising:
   an activation unit for operating the in-vivo device, the activation unit comprising:
      an in-vivo device receiving space for accommodating the in-vivo device housing, and
      a controllable radio frequency radiation source to control the operation of the in-vivo device when the in-vivo device housing is accommodated in the in-vivo device receiving space;
   a data recorder for receiving data from the transceiver of the in-vivo device, said data comprising image data of an image captured using the imaging system of the in-vivo device;
   an in-vivo device association unit to enable communication between the in-vivo device and the data recorder only if the in-vivo device and the data recorder can be associated;
   an in-vivo device functionality test unit to test the performance of the in-vivo device when the in-vivo device housing is accommodated in the in-vivo device receiving space, the in-vivo device functionality test unit comprising a first reference target to produce an optical artifact map of the system, wherein the optical artifact map comprises optical artifacts caused by stray light; and
   an indicator to indicate a result of the test of the in-vivo device functionality performance.

2. The system according to claim 1, wherein the in-vivo device functionality test unit comprises a second reference target to produce an illumination reference map corresponding to the illumination of the illumination source of the in-vivo device.

3. The system according to claim 1, wherein the in-vivo device receiving space is selected from the group comprising an open recess and a light-tight chamber.

4. The system according to claim 1, comprising a processor for determining presence of an artifact in the optical artifact map.

5. The system according to claim 4, wherein the processor is configured to analyze the optical artifact map, and to determine the percentage of faulty areas in the field of view of the in-vivo device.

6. The system according to claim 4, wherein the processor is configured to remove the artifact from a captured image by subtracting the optical artifact map from the captured image.

7. The system according to claim 6, wherein the processor is configured to normalize the optical artifact map prior to the subtraction of the optical artifact map from the captured image, by using the formula, $$I_{out}(x, y) = I_{raw}(x, y) - \frac{G_{raw} \cdot E_{raw}}{G_{optic\_ref} \cdot E_{optic\_ref}} I_{optic\_ref}(x, y)$$

where $I_{out}(x, y)$ is the substantially artifact-free image, $I_{raw}(x, y)$ is the (raw) captured image, $I_{optic\_ref}(x, y)$ is the optical artifact map, $G_{raw}$ is the analog gain level used to capture the image, $E_{raw}$ is the light pulse width used to capture the image, $G_{optic\_ref}$ is the analog gain level used to capture the optical artifact map; and $E_{optic\_ref}$ is the light pulse width used to capture the optical artifact map.

8. The system according to claim 4, wherein the processor is configured to deactivate the in-vivo device and provide a failure indication if the functionality test fails.

9. A method for accommodating and initializing an in-vivo device, said in-vivo device comprising a housing, the in-vivo device housing comprising an imaging system, an illumination source, a transceiver and a radio frequency operable switch, the method comprising the steps of:
for a switched off in-vivo device, wherein the in-vivo device housing is placed in an in-vivo device receiving space of an activation unit,
switching on the in-vivo device by transmitting a radio frequency activation signal from a radio frequency radiation source of the activation unit;
detecting a connection between the radio frequency activation unit and a data recorder;
determining, by using an in-vivo device association unit, whether the data recorder and the activated in-vivo device can be associated, and if the in-vivo device and the data recorder can be associated,
(i) enabling communication between the in-vivo device and the data recorder, and
(ii) testing the functionality of the in-vivo device by using an in-vivo device functionality test unit, the testing comprising obtaining, using the in-vivo device and a reference target of the in-vivo device functionality test unit, an optical artifact map of the system, wherein the optical artifact map comprises optical artifacts caused by stray light, and determining, using a processor, presence of an artifact in the optical artifact map.

10. The method according to claim 9, comprising analyzing the optical artifact map to determine the percentage of faulty areas in the field of view of the in-vivo device.

11. The method according to claim 9, comprising:
removing the artifact from an image captured by the in-vivo device by subtracting the optical artifact map from the captured image.

12. The method according to claim 11, comprising normalizing the optical artifact map prior to the subtraction of the optical artifact map from the captured image.

13. The method according to claim 12, comprising normalizing the optical artifact map according to telemetry data including or representing light gain or exposure time used to capture the image.

14. The method according to claim 12, wherein normalizing the optical artifact map is done using the formula, $$I_{out}(x, y) = I_{raw}(x, y) - \frac{G_{raw} \cdot E_{raw}}{G_{optic\_ref} \cdot E_{optic\_ref}} I_{optic\_ref}(x, y)$$

where $I_{out}(x, y)$ is the substantially artifact-free image, $I_{raw}(x, y)$ is the (raw) captured image, $I_{optic\_ref}(x, y)$ is the optical artifact map, $G_{raw}$ is the analog gain level used to capture the image, $E_{raw}$ is the light pulse width used to capture the image, $G_{optic\_ref}$ is the analog gain level used to capture the optical artifact map; and $E_{optic\_ref}$ is the light pulse width used to capture the optical artifact map.

15. The method according to claim 9, comprising indicating a result of the functionality test.

16. The method according to claim 9, comprising deactivating the in-vivo device if the functionality test fails, and providing a failure indication.

17. The method according to claim 9, wherein testing the functionality of the in-vivo device comprises testing the illumination source by:
obtaining, using the in-vivo device, an illumination reference map by capturing an image of an illumination reference target;
transferring the illumination reference map to the data recorder; and
analyzing the illumination reference map in the data recorder.

18. The method according to claim 17, further comprising:
correcting the illumination intensity of an image based on the illumination reference map.

19. The method according to claim 17, further comprising using the illumination reference map to detect image details in a captured image by using a scene reflectance (S), $$S = a \cdot \frac{I_{out}(x, y)}{I_{illum\_ref}(x, y)} + b$$

where $I_{OUT}$ denotes the captured image, $I_{illum\_ref}$ denotes the illumination reference map, and a and b are constants.

20. The method according to claim 17, comprising comparing the illumination reference map to a predetermined illumination map to determine corrective adjustment and operation of the illumination source.

* * * * *